(12) United States Patent
Hill et al.

(10) Patent No.: US 8,987,194 B2
(45) Date of Patent: Mar. 24, 2015

(54) MUTANT NISIN SER 29 DERIVATIVES AND THE USE THEREOF

(75) Inventors: Colin Hill, Cork (IE); Paul Cotter, Cork (IE); Paul R. Ross, Cork (IE); Desmond Field, Cork (IE)

(73) Assignees: University College Cork-National University of Ireland, Cork, Cork (IE); Agriculture and Food Development Authority, Carlow (IE)

( * ) Notice: Subject to any disclaimer, the term of this patent is extended or adjusted under 35 U.S.C. 154(b) by 0 days.

(21) Appl. No.: 13/517,179

(22) PCT Filed: Dec. 22, 2010

(86) PCT No.: PCT/EP2010/070597
§ 371 (c)(1),
(2), (4) Date: Sep. 4, 2012

(87) PCT Pub. No.: WO2011/076903
PCT Pub. Date: Jun. 30, 2011

(65) Prior Publication Data
US 2013/0005647 A1    Jan. 3, 2013

(30) Foreign Application Priority Data
Dec. 22, 2009 (EP) ..................................... 09180498

(51) Int. Cl.
*A61K 38/16*    (2006.01)
*A61K 38/12*    (2006.01)
*C12N 15/00*    (2006.01)
*C07K 14/315*   (2006.01)
*A61K 38/00*    (2006.01)

(52) U.S. Cl.
CPC ............... *C07K 14/315* (2013.01); *A61K 38/00* (2013.01)
USPC ........ 514/2.9; 530/317; 536/23.7; 435/252.3; 435/320.1

(58) Field of Classification Search
None
See application file for complete search history.

(56) References Cited

U.S. PATENT DOCUMENTS 5,861,275 A * 1/1999 Hansen ........................ 435/69.1

FOREIGN PATENT DOCUMENTS

CN    101691397    *   4/2010   ........... C07K 14/195
CN    101691397 A      4/2010

OTHER PUBLICATIONS

Field et al., The generation of nisin variants with enhanced activity against specific Gram-postitive pathogens, Mol. Micro. (2000 69(1) 218-230 (supplied by Applicant in information Disclosure Statement).*
Field et al., The generation of nisin variants with enhanced activity against specific Gram-positive pathogens, Mol. Microbiol., (2008) 69(1), 218-230.*
Field et al., "The generation of nisin variants with enhanced activity against specific Gram-positive pathogens," Molecular Microbiology 69(11):218-230, 2008.
Rink et al., "Dissection and Modulation of the Four Distinct Activities of Nisin by Mutagenesis of Rings A and B and by C-Terminal Truncation," Applied and Environmental Microbiology, 73(18):5809-5816, Sep. 2007.
Wirawan et al., "Molecular and Genetic Characterization of a Novel Nisin Variant Produced by *Streptococcus uberis*," Applied and Environmental Microbiology, 72(2):1148-1156, Feb. 2006.
Database UniProt [Online], "RecName: Full=Lantibiotic nisin-U; Flags: Precursor; 25 55 Latibiotic nisin-U.", XP0026300035, retrieved from EBI accession No. UNIPORT:Q2QBT0, Database accession No. Q2QBT0 abstract.
Written Opinion for PCT/EP2010/070597, mailed on Aug. 4, 2011, 8 pages.

* cited by examiner

*Primary Examiner* — Karlheinz R Skowronek
*Assistant Examiner* — Joseph Fischer
(74) *Attorney, Agent, or Firm* — K&L Gates LLP

(57) ABSTRACT

A Nisin derivative or variant, comprising an amino acid substitution at amino acid position 29 in the amino acid sequence. The Nisin derivative exhibits enhanced antimicrobial activity when compared to wild type Nisin. The Nisin derivative has an application as a natural food additive and as a therapeutic agent.

33 Claims, 7 Drawing Sheets

SEQUENCE LISTING

```
<160> NUMBER OF SEQ ID NOS: 9

<210> SEQ ID NO 1
<211> LENGTH: 30
<212> TYPE: DNA
<213> ORGANISM: Artificial Sequence
<220> FEATURE:
<223> OTHER INFORMATION: NisS29deg For
<220> FEATURE:
<221> NAME/KEY: misc_feature
<222> LOCATION: (10)..(11)
<223> OTHER INFORMATION: n is a, c, g, or t

<400> SEQUENCE: 1
tgtcattgtn nkattcacgt aagcaaataa                                          30

<210> SEQ ID NO 2
<211> LENGTH: 39
<212> TYPE: DNA
<213> ORGANISM: Artificial Sequence
<220> FEATURE:
<223> OTHER INFORMATION: NisS29deg Rev primer
<220> FEATURE:
<221> NAME/KEY: misc_feature
<222> LOCATION: (11)..(12)
<223> OTHER INFORMATION: n is a, c, g, or t

<400> SEQUENCE: 2
tacgtgaatm nnacaatgac aagttgctgt tttcatgtt                                39

<210> SEQ ID NO 3
<211> LENGTH: 42
<212> TYPE: DNA
<213> ORGANISM: Artificial Sequence
<220> FEATURE:
<223> OTHER INFORMATION: NisZS29deg for primer
<220> FEATURE:
<221> NAME/KEY: misc_feature
<222> LOCATION: (16)..(17)
<223> OTHER INFORMATION: n is a, c, g, or t

<400> SEQUENCE: 3
gcaacttgta actgtnnkat tcacgtaagc aaataatcta ga                            42

<210> SEQ ID NO 4
<211> LENGTH: 42
<212> TYPE: DNA
<213> ORGANISM: Artificial Sequence
<220> FEATURE:
<223> OTHER INFORMATION: NisZS29deg Rev primer
<220> FEATURE:
<221> NAME/KEY: misc_feature
<222> LOCATION: (14)..(15)
<223> OTHER INFORMATION: n is a, c, g, or t

<400> SEQUENCE: 4
gcttacgtga atmnnacagt tacaagttgc tgttttcatg tt                            42
```

<210> SEQ ID NO 5
<211> LENGTH: 42
<212> TYPE: DNA
<213> ORGANISM: Artificial Sequence
<220> FEATURE:
<223> OTHER INFORMATION: NisFS29deg For primer
<220> FEATURE:
<221> NAME/KEY: misc_feature
<222> LOCATION: (16)..(17)
<223> OTHER INFORMATION: n is a, c, g, or t

<400> SEQUENCE: 5
gcaacttgta actgtnnkgt tcacgtaagc aaataatcta ga          42

<210> SEQ ID NO 6
<211> LENGTH: 42
<212> TYPE: DNA
<213> ORGANISM: Artificial Sequence
<220> FEATURE:
<223> OTHER INFORMATION: NisFS29deg Rev primer
<220> FEATURE:
<221> NAME/KEY: misc_feature
<222> LOCATION: (14)..(15)
<223> OTHER INFORMATION: n is a, c, g, or t

<400> SEQUENCE: 6
gcttacgtga acmnnacagt tacaagttgc tgttttcatg tt          42

<210> SEQ ID NO 7
<211> LENGTH: 39
<212> TYPE: DNA
<213> ORGANISM: Artificial Sequence
<220> FEATURE:
<223> OTHER INFORMATION: NisQS29deg Rev primer
<220> FEATURE:
<221> NAME/KEY: misc_feature
<222> LOCATION: (14)..(15)
<223> OTHER INFORMATION: n is a, c, g, or t

<400> SEQUENCE: 7
gcttacgtga acmnnacagt tacaagttgc tgttttcag             39

<210> SEQ ID NO 8
<211> LENGTH: 36
<212> TYPE: DNA
<213> ORGANISM: Artificial Sequence
<220> FEATURE:
<223> OTHER INFORMATION: NisAS29XXdeg For primer
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t

<400> SEQUENCE: 8
tgtcattgtn nknnkcacgt aagcaaataa tctaga                36

<210> SEQ ID NO 9
<211> LENGTH: 42
<212> TYPE: DNA
<213> ORGANISM: Artificial Sequence
<220> FEATURE:
<223> OTHER INFORMATION: NisAS29XXdeg Rev primer
<220> FEATURE:
<221> NAME/KEY: misc_feature
<222> LOCATION: (11)..(12)
<223> OTHER INFORMATION: n is a, c, g, or t

```
<220> FEATURE:
<221> NAME/KEY: misc_feature
<222> LOCATION: (14)..(15)
<223> OTHER INFORMATION: n is a, c, g, or t

<400> SEQUENCE: 9
gcttacgtgm nnmnnacata gacaagttgc tgttttcatg tt                               42
```

MUTANT NISIN SER 29 DERIVATIVES AND THE USE THEREOF

CROSS REFERENCE TO RELATED APPLICATIONS

This application is the national phase under 35 U.S.C. §371 of International Application No. PCT/EP2010/070597, filed on Dec. 22, 2010, which claims priority to and the benefit of European Patent Application No. 09180498.9 filed on Dec. 22, 2009, the entire disclosures of each of which are incorporated by reference herein.

FIELD OF THE INVENTION

The present invention relates to lantibiotics and in particular, to the lantibiotic, Nisin. More specifically, the present invention relates to a derivative of Nisin protein that exhibits enhanced bioactivity against a range of microorganisms, compared to the wild type Nisin protein. The present invention further relates to the application of a Nisin derivative as a natural food additive and as a therapeutic agent.

BACKGROUND TO THE INVENTION

Lantibiotics are gene-encoded, ribosomally synthesized derived peptides that have attracted widespread scientific attention in recent years, not only as promising safe and natural food additives, but also as potential therapeutic agents, such as chemotherapeutic agents. Lantibiotics are produced by a large number of gram-positive bacteria and are considered members of a group of bacterial toxins called bacteriocins. The original and most intensively studied lantibiotic is the Nisin lantibiotic.

Nisin is a polycylic, 34 amino acid peptide with antibacterial activity against a range of gram-positive bacteria and a small number of gram-negative bacteria. These include food-borne pathogens, such as staphylococci, bacilli, clostridia and mycobacteria. Nisin A, a natural variant of Nisin, was first marketed in England in 1953 and is FDA approved with a long record of safe use (Delves Broughton, 1990). Nisin A is one of only a few bacteriocins to have been applied commercially (Twomey et al., 2002). To date, six natural variants of Nisin have been identified. These variants are Nisin A (Kaletta and Entian, 1989), Nisin Z (Mulders et al., 1991), Nisin Q (Zendo et al., 2003) and Nisin F (de Kwaadsteniet et al., 2007) which are produced by starter *Lactococcus lactis* species, while Nisin U and Nisin U2 are produced by *Streptococcus uberis* (Wirawan et al., 2006).

Studies investigating the mode of action of lanitbiotics have revealed the membrane-bound peptidoglycan precursor lipid II to be the docking molecule for the Nisin lantibiotic. The binding of Nisin to lipid II facilitates two bactericidal activities, namely, membrane pore formation and the inhibition of peptidoglycan biosynthesis (Bonelli et al., 2006; Breukink et al., 1999; Brotz et al., 1998; Wiedemann et al., 2001). The dual activity of Nisin is thought to be due to the presence of two-structural domains located at the N- and C-termini respectively. The N-terminal domain contains three post-translationally incorporated (β-methyl) lanthionine rings (rings A, B, and C) and is linked to the C-terminal rings (rings D and E) by a flexible region, or hinge. It has been established that the A, B and C rings of the N-terminal form a 'cage', that facilitates binding to the pyrophosphate moiety of lipid II, thus interfering with the process of cell wall synthesis (Hsu et al., 2004). This binding in turn enhances the ability of the C-terminal segment, containing rings D and E, to form pores in the cell membrane, resulting in the rapid efflux of ions and cytoplasmic solutes, such as amino acids and nucleotides, into the cell (Wiedemann et al., 2001).

Nisin's commercial use in the food industry stems from its ability to suppress gram-positive spoilage and other pathogenic bacteria. It also possesses low anti-gram-negative activity, which increases when combined with other hurdles e.g. high pressure, EDTA chelation, freezing, heating, low pH etc. The use of Nisin is likely to increase in the coming years due to the increased consumer demand for minimally processed foods lacking chemical preservatives.

Nisin is also used in the veterinary industry and has been shown to inhibit the gram positive pathogenic bacteria responsible for bovine mastitis including *Streptococcus agalactiae, Strep. dysgalactiae, Strep. uberis* and *Staphylococcus aureus*. Bovine mastitis is an inflammation of the udder that is both persistent and costly to treat. Consequently, in recent years Nisin has been incorporated into a number of commercial products that are used as an alternative treatment for bovine mastitis (Sears et al., 1992; Wu et al., 2007). For example, Immucell produce Wipe Out®, used to clean and sanitize the teat area before and after milking. This successfully reduced levels of the mastitis pathogens *Staph. aureus* (99.9%), *Strep. agalactiae* (99.9%), *E. coli* (99%), *Step. uberis* (99%) and *Klebsiella pneumoniae* (99%) in experimental exposure studies (J. Dairy Sci 75:3185-3192). Mast Out®, a Nisin-based treatment for mastitis in lactating cows has been shown to give statistically significant cure rates in an experimental field trial involving 139 cows with subclinical mastitis. Similarly, another lantibiotic, lacticin 3147, has been successfully incorporated into a teat seal product with a view to protecting the seal during the 'drying-off' period.

Nisin inhibits a number of pathogenic microbes. The effectiveness of Nisin against enterococci and staphylococci and mycobacteria has been shown, as has its activity against *Clostridium difficile*.

Lantibiotics are generally regarded as possessing poor anti-gram-negative activity. This insensitivity is thought to be due to the inability of the lantibiotic to pass across the outer membrane of the gram-negative cell wall, thus limiting access to lipid II. However, this general trend is not always strictly true. In fact, it has been established that in its purified form, Nisin Z exhibits activity against other gram-negative microbes such as *Escherichia coli* and *S. aureus*. Both Nisin A and Z exhibited activity against two antibiotic resistant strains of gram negative *Neisseria gonorrhoeae* and *Helicobacter pylori*. Another gram-negative bacteria that has shown susceptibility to Nisin (whether alone or in combination with other antimicrobials) is *Pseudomonas aeruginosa*. It should be understood that small amounts of the Nisin peptide may pass through the outer membrane of these targets and, furthermore, this activity can be further enhanced when used in combination with other compounds that disrupt this outer membrane.

In yet another application, Nisin has also been shown to have potential as a contraceptive.

It has been demonstrated in laboratory settings that bacteria can become resistant to Nisin, e.g. serial exposure of a penicillin-susceptible strain of *Strep. pneumoniae* to Nisin (1 mg/L) in liquid culture resulted in the rapid appearance of stable Nisin-resistant mutants in which the minimum inhibitory concentration (MIC) increased from 0.4 to 6.4 mg/L (Severina, 1998). In these spontaneous mutants, resistance correlates with cell envelope changes such as alterations in membrane charge and fluidity (Li, 2002; Verheul, 1997), cell wall thickness (Maisnier-Patin, 1996), cell wall charge (Mantovani, 2001; Abachin, 2002; Bierbaum, 1987) and combinations thereof (Crandall, 1998), arising following direct exposure to a low level of lantibiotic or as part of an adaptive response to another stress (van Schaik, 1999). The specific mechanism(s) by which cells become resistant to Nisin is not well understood although it is apparent that variations in the lipid II content are not responsible (Kramer, 2004). Genetic loci associated with the development of enhanced Nisin resistance (Cotter, 2002; Gravesen, 2004; Gravesen, 2001) or an innate tolerance of Nisin, have been identified (Peschel, 1999; Abachin, 2002; Cao, 2004). In the latter example, the cell envelope charge would seem to be the most important consideration. While this has not as yet impacted on the application of Nisin in the food industry, it has implications for applications in the future and the potential of Nisin as a clinical antimicrobial. This however, does point to the importance of identifying further antimicrobials, including variants of existing antimicrobials, to overcome resistance problems.

The diversity of the Nisin natural variants highlights the ability of certain residues and domains within the molecule to tolerate change. However, comparisons between closely (e.g. subtilin) and more distantly related (e.g. epidermin) lantibiotics revealed that highly conserved elements, with essential structure/function roles, also exist.

Despite the relatively plastic nature of the Nisin peptides and of the bioengineered derivatives of Nisin that have been generated and characterized to date, only a limited number (for example, T2S and M17Q/G18T) display increased activity against at least one gram-positive bacteria, and even then, activity is enhanced only with respect to a limited number non-pathogenic indicator strains (*Micrococcus flavus* or *Streptococcus thermophilus*) (Cotter et al., 2005a; Lubelski et al., 2007; Siezen et al., 1996). A recent study by Rink et al, involving the randomization of an N-terminal domain fragment of the Nisin peptide, reported enhanced $IC_{50}$s against specific indicator strains (Rink et al., 2007b).

Nisin A is a cationic antimicrobial peptide due to the presence of 5 positively charged residues (Lys12, Lys22, Lys34, His27, His31) and the absence of negatively charged residues. The consequences of charge manipulation to date have been variable. Yuan et al, 2004 disclosed that the incorporation of negatively charged residues had a detrimental impact (e.g. the hinge mutants N20E, M21E and K22E) and subsequently revealed that the introduction of positively charged residues had a more beneficial outcome with respect to anti-gram-negative activity, (N20K and M21K). A further unusual feature of the Nisin lantibiotic is the absence of aromatic residues. To date all aromatic residue-containing forms of Nisin have been bioengineered derivatives and all have displayed reduced antimicrobial activity (i.e. I1W, M17W, V32W, I30W, N20F and N20F/M21L/K22Q (Breukink et al., 1998; Martin et al., 1996; Yuan et al., 2004). Hasper et al, and Wiedemann et al, both established that proline incorporation (i.e. N20P/M21P), resulted in the generation of a Nisin peptide incapable of pore formation. A number of small amino acids have previously been introduced into the hinge region of Nisin Z, including M21G (slightly reduced activity), K22G (slightly reduced activity) and N20A/K22G (as part of an epidermin-like hinge N20A/M21K/Dhb/K22G, greatly reduced activity); (Yuan et al., 2004). It has further been reported by Yuan et al, that an N20Q substitution in Nisin Z results in slightly diminished activity (Yuan et al., 2004). In 2008, Field et al., generated the largest bank of randomly mutated Nisin derivatives reported to date, with the ultimate aim of identifying variants with enhanced bioactivity. This approach led to the identification of a Nisin-producing strain with enhanced bioactivity against the mastitic pathogen *Streptococcus agalactiae* resulting from an amino acid change in the hinge region of the peptide (K22T). Prompted by this discovery, site-directed and site-saturation mutagenesis of the hinge region residues was employed, resulting in the identification of additional derivatives, most notably N20P, M21V and K22S, with enhanced bioactivity and specific activity against Gram-positive pathogens including *Listeria monocytogenes* and/or *Staphylococcus aureus*. The identification of these derivatives represents a major step forward in the bioengineering of Nisin and lantibiotics in general.

Wirawan et al established that the natural Nisin variants Nisin U and Nisin U2 differ from Nisin A with respect to a number of different amino acids. Chan et al reported that the removal of the C-terminal five residues and a further nine residues, from Nisin to produce Nisin 1-29 or Nisin 1-20, respectively, leads to a 16 fold or 110 fold decrease in bactericidal potency, respectively, compared with that of intact Nisin. Additionally, Sun et al reported that Nisin 1-28 also showed a 100 fold reduced inhibitory activity against *L. lactis* MG1363.

Prior to the priority date of the present invention (22 Dec. 2009), no Nisin variants have been reported in which Ser 29 position has been bioengineered. Natural variants such as Nisin U and U2, differ with respect to this location, i.e. contain a natural Ser29His variation, but also contain a number of additional amino acid changes. Thus, the specific significance of the His amino acid change at position 29 is not known. These, and indeed the majority of bioengineered peptides generated to date, have resulted from site-directed approaches, with random bioengineering of the intact Nisin peptide being carried out only on a relatively small scale only. Furthermore, these studies have been largely unsuccessful, yielding derivatives with reduced or absent antimicrobial activity.

Published in April 2010, Chinese Patent Application Publication No. CN101691397 documents a Nisin Z mutant variant having S29A change, in which the serine at the 29 position is replaced by alanine. This mutant Nisin Z protein is said to have broader bacteriostatic spectrum for inhibition of gram-positive bacteria such as *Micrococcus flavus, Streptococcus pneumoniae* and *Staphylococcus epidermidis*. This Nisin Z mutant is also reported to have a higher stability compared to wild Nisin.

The recognition of resistance to lantibiotics such as Nisin is growing, a factor which contributes to the urgent need for alternative antimicrobial peptides that exhibit a superior antimicrobial activity towards gram-positive bacteria. There is thus a need for additional alternative anti-microbial agents, which would be effective against strains that are insensitive to Nisin. The use of Nisin is likely to increase in the coming years due to the increased customer demand for minimally processed foods lacking chemical preservatives. Nisin is also used in the veterinary industry and has potential as a clinical antimicrobial. Despite its general efficacy there exist specific isolates and species of bacteria that are not effectively controlled by Nisin.

The invention described herein relates to a set of Nisin derivatives, which possess enhanced antimicrobial activity. Such bioengineered Nisin derivatives demonstrating enhanced activity against specific target strains and producers thereof have a variety of food, veterinary and clinical applications.

OBJECT OF THE INVENTION

It is an object of the current invention to provide an alternative antimicrobial agent or a producer thereof, with enhanced bioactivity.

In particular, it is an object of the current invention to provide an agent or producer thereof, with enhanced bioactivity against gram-positive pathogens and/or gram negative pathogens.

In particular, it is an object of the current invention to provide a derivative or variant of the lantibiotic Nisin, displaying enhanced activity against gram-positive and/or gram-negative organisms, particularly against strains of clinical or food relevance.

A further object of the current invention is the use of a Nisin derivative in the manufacture of a medicament to treat disease. The disease may be selected from the group consisting of, but not limited to, bovine mastitis, oral infections including dental plaque, gastric ulcers, CDAD (*Clostridum difficile* associated diarrhoea) and acne.

It is a still further object of the invention to provide the use of a Nisin derivative as a food additive or a food preservative.

It is an additional object of the invention to provide a pharmaceutical composition comprising Nisin derivatives for use in the treatment and prevention of infections caused by gram-positive and/or gram-negative organisms. The pharmaceutical composition can be adapted for use in food/cheese/beverages or it may be formulated with conventional carriers or excipients as oral capsules, intravenously administrable compositions, suppositories, topical creams or ointments or the like

SUMMARY OF THE INVENTION

In the first aspect of the invention there is provided a mutant of a natural Nisin variant comprising an amino acid substitution resulting in a G, A, E, D, C, M, Q, R, V, P, W, T, N, I, L, H, K, Y or an F amino acid at the 29 position of the amino acid sequence, wherein the Nisin mutant exhibits an antimicrobial activity compared to wild type Nisin, wherein Nisin Z Ser29Ala is excluded.

The antimicrobial agent of the invention is a mutant derivative of the lantibiotic Nisin. The mutant of a number of Nisin variants has activity as an antimicrobial agent. By derivative it is meant a mutant of Nisin or a mutant of a natural Nisin variant.

The derivative of the Nisin variant may have increased or enhanced antimicrobial activity when compared to wild type Nisin. In other words, a lower concentration of the Nisin derivative is required to inhibit the growth of a microorganism, than the wild type Nisin. Thus, the invention provides a library of Nisin antimicrobial agents or a producer thereof, with enhanced bioactivity. Preferably bioactivity relates to bacteristatic activity which inhibits bacteria function. Most preferably of all, bioactivity refers to bactericidal activity which kills bacteria.

Suitably, the derivative of Nisin may be selected from the group of Nisin variants consisting of: Nisin A, Nisin Z, Nisin F and Nisin Q. Preferably, the derivative is of a Nisin variant selected from Nisin A, Nisin F and Nisin Q. More preferably still, the derivative is of a Nisin variant Nisin A. In one embodiment, a preferred derivative is of a Nisin variant Nisin Z. In another embodiment, the derivative is of a Nisin variant Nisin F. In another embodiment still, the derivative is of a Nisin variant Nisin Q. The choice of Nisin variant will typically depend on the desired application and microbes against which activity is desired.

The Nisin derivative may comprise at least one amino acid substitution or mutation in the amino acid sequence. Preferably, the amino acid substitution is at amino acid position 29 in the amino acid sequence of a particular variant of the Nisin peptide. Suitably, the 29 position of the variant may comprise any one of an amino acid selected from the group consisting of: G, A, E, D, C, M, Q, R, V, P, W, T, N, I, L, H, K, Y and F.

Suitably, the 29 position of the variant may consist of G.
Suitably, the 29 position of the variant may consist of A.
Suitably, the 29 position of the variant may consist of E.
Suitably, the 29 position of the variant may consist of D.
Suitably, the 29 position of the variant may consist of C.
Suitably, the 29 position of the variant may consist of M.
Suitably, the 29 position of the variant may consist of Q.
Suitably, the 29 position of the variant may consist of R.
Suitably, the 29 position of the variant may consist of V.
Suitably, the 29 position of the variant may consist of P.
Suitably, the 29 position of the variant may consist of W.
Suitably, the 29 position of the variant may consist of T.
Suitably, the 29 position of the variant may consist of N.
Suitably, the 29 position of the variant may consist of I.
Suitably, the 29 position of the variant may consist of L.
Suitably, the 29 position of the variant may consist of H.
Suitably, the 29 position of the variant may consist of K.
Suitably, the 29 position of the variant may consist of Y.
Suitably, the 29 position of the variant may consist of F.

The substitution at amino acid position 29 may be in any form of Nisin, i.e. Nisin A, U, U2, Z, F or Q. However, the U and U2 variants are less preferred, as they are quite difficult to bioengineer and less relevant structurally in the context of the invention. Therefore in a particularly preferred embodiment, the Nisin variant may be anyone selected from the group of variants comprising Nisin A, Z, F and Q. Suitably, the Nisin variant may be Nisin A. Suitably, the Nisin variant may be Nisin Z. Suitably, the Nisin variant may be Nisin F. Suitably, the Nisin variant may be Nisin Q. In the case where the Nisin variant is Nisin Z, the amino acid substitution at the Serine 29 position may not be Alanine (A). Thus the Nisin Z Ser29Ala mutant per se is excluded, as are vectors, cell lines containing gene encoding for this particular mutant. However, the use of this mutant in bacteriocidal applications is contemplated by the invention. Use of this mutant against gram-negative bacterial and applications involving gram negative bacteria are also comtemplated.

The amino acid substitution in the amino acid sequence of any of the Nisin peptide variants may be selected from the substitutions listed in Table 1, Table 1A or Table, shown below. Table 1 also lists the corresponding nucleotide changes, which result in the amino acid mutation at the 29 position. While the table refers to any Nisin variant, the skilled person will appreciate that the nucleotide changes for the given position are identical to those that would be used in any desired variant, with the exception of changes that would result in the Nisin Z Ser29Ala mutant, which is exclude per se from the scope of the invention.

TABLE 1

Mutations/substitutions of the Nisin derivatives of the current invention (all mutants identified and by mass spectroscopy and/or sequence analysis).

| Nisin amino acid mutation at position 29 | Nucleotide change(s) |
|---|---|
| Nisin S29G | AGT, AGC to GGT, GGG, GGA, or GGG |
| Nisin S29A | AGT, AGC to GCT, GCC, GCA or GCG |
| Nisin S29E | AGT, AGC to GAG or GAA |
| Nisin S29D | AGT, AGC to GAT or GAC |
| Nisin S29C | AGT, AGC to TGT |
| Nisin S29M | AGT, AGC to ATG |

TABLE 1-continued

Mutations/substitutions of the Nisin derivatives of the current invention (all mutants identified and by mass spectroscopy and/or sequence analysis).

| Nisin amino acid mutation at position 29 | Nucleotide change(s) |
|---|---|
| Nisin S29Q | AGT, AGC to CAA or CAG |
| Nisin S29R | AGT, AGC to CGT, CGC, CGA, CGG, AGA, or AGG |
| Nisin S29V | AGT, AGC to GTT, GTC, GTA or GTG |
| Nisin S29P | AGT, AGC to CCT, CCC, CCA, CCG |
| Nisin S29W | AGT, AGC to TGG |
| Nisin S29T | AGT, AGC to ACT, ACC, ACA, or ACG |
| Nisin S29N | AGT, AGC to AAT or AAC |
| Nisin S29I | AGT, AGC to ATT, ATC or ATA |
| Nisin S29L | AGT, AGC to CTT, CTC, CTA, CTG, TTA or TTG |
| Nisin S29H | AGT, AGC to CAC, or CAT |
| Nisin S29K | AGT, AGC to AAA, or AAG |
| Nisin S29Y | AGT, AGC to TAT, or TAC |
| Nisin S29F | AGT, AGC to TTT, or TTC |

(Ser29 in Nisin A corresponds to the codon AGT; in Nisin F and Nisin Q, the Ser corresponds to AGC; Serine codons corresponding to TCT, TCC, TCA, TCG are proposed)

Mutations, other than the above, which also change the nature of the residue are also relevant. A skilled person in the art will appreciate, that alternative nucleotide substitutions yielding equivalent amino acid changes are possible.

Suitably, the amino acid substitutions at amino acid position Serine (S) 29 of the Nisin peptide variant may be any amino acid substitution selected from the group consisting of: Glycine (G), Alanine (A), Glutamate (E) or Aspartate (D), Glutamine (Q), Arginine (R), Valine (V), Proline (P), Tryptophan (W), Threonine (T), Asparagine (N), or Isoleucine (I), Leucine (L), Cysteine (C), Methionine (M), Histidine (H), Lysine (K), Tyrosine (Y), Phenylalanine (F) and equivalents thereof. For some variants, these substitutions do not lead to enhanced activity for some strains and so are less preferred. These will be apparent from the description below.

Preferably, the amino acid substitutions at amino acid position Serine (S) 29 of the Nisin variant peptide are selected from the group consisting of: Glycine (G), Alanine (A), Glutamate (E), Aspartate (D), Cysteine (C), or Methionine (M) or equivalents thereof. For some variants, these substitutions do not lead to enhanced activity for some strains and so are less preferred, for example Cysteine (C), or Methionine (M) in examples below. These will be apparent from the description below. Thus, in one embodiment, a particularly preferred mutant arises wherein the amino acid substitution results in a Glycine (G), Alanine (A), Aspartate (D), Glutamine (E), Arginine (R), Asparagine (N) or Valine (V) at amino acid position 29 of the amino acid sequence. Most preferred are amino acid substitutions at the Serine 29 position of Arginine (R), Asparagine (N), and Valine (V). For some variants, these substitutions do not lead to enhanced activity for some strains and so are less preferred. These will be apparent from the description below.

In one embodiment the preferred amino acid substitution is Glycine (G).

In one embodiment the preferred amino acid substitution is Alanine (A)

In one embodiment the preferred amino acid substitution is Glutamate (E).

In one embodiment the preferred amino acid substitution is Aspartate (D).

In one embodiment the preferred amino acid substitution is Glutamine (Q).

In one embodiment the preferred amino acid substitution is Arginine (R).

In one embodiment the preferred amino acid substitution is Valine (V).

In one embodiment the preferred amino acid substitution is Proline (P).

In one embodiment the preferred amino acid substitution is Tryptophan (W).

In one embodiment the preferred amino acid substitution is Threonine (T).

In one embodiment the preferred amino acid substitution is Asparagine (N).

In one embodiment the preferred amino acid substitution is Isoleucine (I).

In one embodiment the preferred amino acid substitution is Leucine (L).

In one embodiment the preferred amino acid substitution is Cysteine (C).

In one embodiment the preferred amino acid substitution is Methionine (M).

In one embodiment the preferred amino acid substitution is Histidine (H).

In one embodiment the preferred amino acid substitution is Lysine (K).

In one embodiment the preferred amino acid substitution is Tyrosine (Y).

In one embodiment the preferred amino acid substitution is Phenylalanine (F).

The mutant Nisin variants as described herein, which comprise an amino acid substitution at amino acid position 29 in the amino acid sequence exhibit an antimicrobial activity compared to wild type Nisin and wherein the antimicrobial activity is against gram-positive bacteria and/or gram-negative bacteria. Thus, the mutant Nisin variants as described herein may be used as an antibacterial.

The Nisin derivatives of the current invention display an increased antimicrobial activity against a range of bacterial species compared to the wild type form of the Nisin variant without a mutation or substitution at, at least amino acid position 29.

Suitably, the bacterial species are gram-positive organisms. Advantageously, the mutants may be used against gram-negative bacteria. Such enhanced anti gram-negative activity is a surprising find considering to the lack of such activity for the natural strains. Importantly, this anti gram-negative activity is without the need for simultaneous compounds/conditions that disrupt bacterial cell membranes. The skilled person will appreciate that if such cell membrane disruption is initiated, the mutants of the invention will display further activity.

It is expected that the mutant Nisin variants as described herein show antimicrobial activity against at least one gram-positive bacteria selected from the group consisting of: lactococci, lactobacilli, carnobacteria, enterococci, streptococci, bacilli, clostridia, *Listeria*, staphylococci, propionibacteria, *corynebacteria, eubacterium*, mycobacteria and micrococci, with the exception that where the mutant is Nisin Z Ser29Ala, use against *Micrococcus flavus, Streptococcus pneumoniae* and *Staphylococcus epidermidis* is excluded.

More specifically, the antimicrobial activity is expected against at least one gram-positive bacteria selected from the group consisting of: *L. lactis, L. monocytogenes, L. innocua, E. faecium, E. faecalis, E. durans, S. aureus, S. epidermidis, S. pyogenes, S. pneumoniae, S. mutans, S. agalactiae, S. dysgalactiae, B. cereus, B. firmus, B. licheniformis, B. stearo-*

*thermophilus, B. thuringiensis, B. subtilis, C. sporogenes, C. perfringens, C. difficile, P. acnes, M. tuberculosis, M. avium* subsp. *paratuberculosis, M. luteus, M. flavus*, with the exception that where the mutant is Nisin Z Ser29Ala, use against *Micrococcus flavus, Streptococcus pneumoniae* and *Staphylococcus epidermidis* is excluded.

The inventors have shown that the mutant Nisin variants show enhanced activities against gram-positive bacteria selected from the group consisting of: *L. monocytogenes*, MRSA, *S. aureus, C. difficile, L. lactis, C. sporogenes, B. cereus, Strep. galactiae*, VISA, *S. epidermidis, S. hominis, Bacillus firmus, Strep. dysgalactiae, Strep. mutans*, VRE, *Enterococcus durans, Propionibacterium acnes* and *Micrococcus luteus*, with the exception that where the mutant is Nisin Z Ser29Ala, use against *Staphylococcus epidermidis* is excluded.

It is expected that the mutant Nisin variants as described herein show antimicrobial activity against at gram-negative bacteria selected from the group consisting of: *C. sakazakii, Escherichia coli, Shigella flexneri, Salmonella enteritidis, Pseudomonas aeruginosa, Campylobacter jejuni, Campylobacter coli, Hemophilus influenzae, Klebsiella pneumoniae, Legionella pneumophila, Proteus mirabilis, Enterobacter cloacae, Serratia marcescens, Helicobacter pylori, Salmonella typhi, Acinetobacter baumannii, Yersinia enterocolitica, Aeromonas hydrophila, Bacteroides fragilis, Bacteroides* spp., *Prevotella* spp., *Porphyromonas* spp. and *Fusobacterium* spp.

More specifically, the antimicrobial activity is expected against gram-negative organisms selected from the group consisting of: *Escherichia coli, Salmonella enteritidis, Pseudomonas aeruginosa, Campylobacter jejuni, Campylobacter coli, Hemophilus influenzae, Klebsiella pneumoniae, Legionella pneumophila, Proteus mirabilis, Enterobacter cloacae, Serratia marcescens, Helicobacter pylori, Salmonella typhi, Acinetobacter baumannii* and *Cronobacter sakazakii*.

In particular, gram-negative organisms are preferably *Cronobacter sakazakii*.

For some mutant variants, these substitutions do not lead to enhanced activity for some strains and so are less preferred. These will be apparent from the description below.

In particular, the following uses are preferred:
Nisin A S29G, S29A, S29R mutants against *L. monocytogenes*,
Nisin A S29G, S29A, S29D, S29E, Nisin Z S29G, NisinQ S29A against *S. aureus*,
Nisin A S29G, S29A, S29D against MRSA,
Nisin A S29G, S29A, S29E against VISA,
Nisin A S29G, Nisin A S29A against *S. epidermidis*,
Nisin A S29G, Nisin A S29A, Nisin A S29D against *S. hominis*,
Nisin A S29G, S29A, S29D, S29E, Nisin Z S29G, S29D, S29E, S29N, Nisin F S29A, S29E, S29V, S29N, Nisin Q S29A, S29D, S29E, S29P against *L. lactis*,
Nisin A S29G, S29A against *B. cereus*,
Nisin A S29A, S29D against *Bacillus firmus*,
Nisin A S29G, Nisin A S29A, Nisin A S29D against *Strep. agalactiae*,
Nisin A S29G, Nisin A S29A, Nisin A S29D, Nisin A S29E against *Strep. dysgalactiae*,
Nisin A S29G, Nisin A S29A, Nisin A S29D, Nisin A S29E against *Strep. mutans*,
Nisin A S29G, Nisin A S29A, Nisin A S29D, Nisin A S29E against VRE,
Nisin A S29G, Nisin A S29A, Nisin A S29D, Nisin A S29E against *Enterococcus durans*,
Nisin A S29G, Nisin A S29D, Nisin A S29E against *Propionibacterium acnes*, and
Nisin A S29G, Nisin A S29D against *Micrococcus luteus*.

Suitably, the amino acid substitution at position Serine (5) 29 may be Glycine (G), wherein the Nisin variant is Nisin A. This Nisin A S29G mutant is particularly useful against *L. monocyotgenes, L. lactis, S. aureus, S. hominis, S. epidermidis, S. agalactiae, S. dysgalactiae, S. mutans*, Vancomycin resistant *Enterococcus, E. faecium* and *E. durans* 5133, *P. acnes, B. cereus, M luteus* and *C. sakazakii*.

Suitably, the amino acid substitution at position Serine (5) 29 may be Alanine (A), wherein the Nisin variant is Nisin A. This Nisin A S29A mutant is particularly useful against *L. lactis, S. aureus, S. hominis, S. epidermidis, S. mutans, S. agalactiae, Enterococcus durans, Enterococcus faecium, Bacillus cereus, Bacillus firmus, Enterococcus durans, L. monocytogenes* LO28 and *C. sakazakii*

Suitably, the amino acid substitution at position Serine (S) 29 may be Aspartate (D), wherein the Nisin variant is Nisin A. This Nisin A S29D mutant is particularly useful against *L. lactis, S. aureus, S. hominis* IMF12, *S. agalactiae, S. mutans, S. dysgalactiae* 43078, Vancomycin resistant *Enterococcus, E. faecium, E. durans, P. acnes, B. firmus, M. luteus* and *C. sakazakii*.

Suitably, the amino acid substitution at position Serine (S) 29 may be Glutamate (E), wherein the Nisin variant is Nisin A. This Nisin A S29E mutant is particularly useful against *L. lactis, S. aureus, S. dysgalactiae, S. mutans*, Vancomycin resistant *Enterococcus, E. durans, P. acnes* and *C. sakazakii*.

Suitably, the amino acid substitution at position Serine (S) 29 may be Glycine (G), wherein the Nisin variant is Nisin Z. This Nisin Z S29G mutant is particularly useful against *S. aureus* and *L. lactis*.

Suitably, the amino acid substitution at position Serine (S) 29 may be Aspartate (D), wherein the Nisin variant is Nisin Z. This Nisin Z S29D mutant is particularly useful against *L. lactis*.

Suitably, the amino acid substitution at position Serine (S) 29 may be Glutamate (E), wherein the Nisin variant is Nisin Z. This Nisin Z S29E mutant is particularly useful against *L. lactis*.

Suitably, the amino acid substitution at position Serine (S) 29 may be Alanine (A), wherein the Nisin variant is Nisin F. This Nisin F S29A mutant is particularly useful against *L. lactis*.

Suitably, the amino acid substitution at position Serine (S) 29 may be Glutamate (E), wherein the Nisin variant is Nisin F. This Nisin F S29E mutant is particularly useful against *L. lactis*.

Suitably, the amino acid substitution at position Serine (S) 29 may be Alanine (A), wherein the Nisin variant is Nisin Q. This Nisin Q S29A mutant is particularly useful against *L. lactis* and *S. aureus*.

Suitably, the amino acid substitution at position Serine (S) 29 may be Aspartate (D), wherein the Nisin variant is Nisin Q. This Nisin Q S29D mutant is particularly useful against *L. lactis*.

Suitably, the amino acid substitution at position Serine (S) 29 may be Glutamate (E), wherein the Nisin variant is Nisin Q. This Nisin Q S29E mutant is particularly useful against *L. lactis*.

Suitably, the amino acid substitution at position Serine (S) 29 may be Arginine (R), wherein the Nisin variant is Nisin A. This Nisin A S29R mutant is particularly useful against *Listeria monocytogenes* and *Cronobacter sakazakii*.

Suitably, the amino acid substitution at position Serine (S) 29 may be Asparagine (N), wherein the Nisin variant is Nisin Z and/or Nisin F. The Nisin Z S29N mutant is particularly useful against L. lactis HP. The Nisin F S29N mutant is particularly useful against L. lactis HP.

Suitably, the amino acid substitution at position Serine (S) 29 may be Valine (V), wherein the Nisin variant is Nisin F. The Nisin F S29V mutant is particularly useful L. lactis HP.

Suitably, the amino acid substitution at position Serine (S) 29 may be Proline (P), wherein the Nisin variant is Nisin Q. The Nisin F S29P mutant is particularly useful L. lactis HP.

In the case where the variant is the Nisin Z variant, mutation at the 29 position cannot be Alanine (A).

The skilled person will appreciate that the advantages arising from Nisin variants having Serine-29 mutations may still arise where other substitutions are made to the Nisin variant amino acid sequence. In other words, included within the scope of the invention are all Nisin Serine-29 mutants with at least one further amino acid sequence substitutions wherein the advantageous activity is retained.

In a related aspect, the Nisin variant mutants may comprise at least one further amino acid substitution at amino acid position 30 in the amino acid sequence. Thus, the Nisin variant may be derivatized to comprise two mutations or more mutations in the peptide chain. Suitably, for example, a double mutants arises wherein the amino acids at the 29 and 30 positions are altered simultaneously. Suitably, double mutants arises wherein the amino acid substitution results in a Glycine (G), Alanine (A), Aspartate (D), Glutamine (E), Arginine (R), Asparagine (N) or Valine (V) at amino acid position 29 of the amino acid sequence and wherein the further amino acid substitution results in a Valine (V), Leucine (L), Isoleucine (I), Alanine (A), Glycine (G) at amino acid position 30 of the amino acid sequence. Most preferably, the double mutants comprise an A, D, E or N at the 29 position. Suitably, the 30 position comprises a V, L, I, A, or G substitution.

Any combinations of these substitutions are contemplated and are expected to show antimicrobial activity. Particularly preferred double mutants are shown below in Table 1A, as are their activities against the bacteria indicated.

| Serine29X | Isoleucine30X | L. lactis HP | S. aureus RF122 | L. mono LO28 |
|---|---|---|---|---|
| D | V | ✓ | | |
| D | L | ✓ | | |
| D | I | ✓ | ✓ | ✓ |
| A | V | | ✓ | |
| E | L | ✓ | ✓ | ✓ |
| E | A | ✓ | | |
| S | G | ✓ | | |
| S | V | ✓ | ✓ | ✓ |
| N | L | ✓ | | |

Suitably, the gram-positive organisms are selected from the group consisting of bacilli, clostridia, mycobacteria, S. aureus including met(h)icillin resistant (MRSA), vancomycin insensitive (VISA) and heterogeneous vancomycin insensitive (hVISA) forms, Listeria, enterococci including vancomycin resistant (VRE) forms, lactobacilli, lactococci, propionibacteria, micrococci and streptococci. In another embodiment, gram-positive organisms clostridia is expected to be susceptible. The gram positive bacteria may be selected from the group consisting of: L. monocyotgenes 10403s, L. monocyotgenes EGDe ΔvirR, L. monocytogenes EGDe Δmprf, L. monocytogenes LO28, Lactococcus lactis MG1363, L. lactis HP, S. hominis IMF12, Staphylococcus aureus SA113, S. aureus DPC 5247, S. aureus NCD1499, S. aureus RF122, S. aureus Newman, S. aureus 528 (MRSA), S. aureus 530 (MRSA), S. aureus 523 (MRSA), S. epidermidis IMF54, hVISA32652, hVISA32679, Streptococcus agalactiae ATCC13813, Streptococcus dysgalactiae 43078, and Streptococcus mutans, Vancomycin resistant Enterococcus VRE Ec520, VRE Ec295, VRE Ec533, VRE Ec725, VRE Ec538, Enterococcus faecium IMF91, Enterococcus durans 5133, Enterococcus durans IMF90, Propionibacterium acnes, Bacillus cereus IMF4, Micrococcus luteus. Bacillus cereus DPC 6088 and Bacillus firmus IMF68.

Suitably, the gram negative bacteria may be selected from the group consisting of C. sakazakii DPC 6440, C. sakazakii DPC 6441, C. sakazakii DPC 6442, C. sakazakii DPC 6443, C. sakazakii DPC 6444, C. sakazakii DPC 6448, C. sakazakii DPC 6522, C. sakazakii DPC 6524, C. sakazakii DPC6440, C. sakazakii DPC6442 and C. sakazakii DPC6446.

Table 2 lists a number of Nisin variant mutant derivatives of Nisin A, Z, F and Q of the current invention, all of which contain substitutions at amino acid position 29 of the Nisin peptide. Enhanced bioactivity against the strains listed is observed when compared to wild type Nisin with no amino acid substitution at amino acid position 29 (i.e. deferred antagonism agar-based overlay assays) against the strains listed. The Nisin Z Ser29Ala mutant per se is excluded.

TABLE 2

Nisin derivatives with enhanced bioactivity

| | Strain |
|---|---|
| Nisin A Derivative | |
| Nisin S29G | Gram Positive: L. monocyotgenes 10403s, L. monocyotgenes EGDe ΔvirR and L. monocytogenes EGDe Δmprf, Lactococcus lactis MG1363, L. lactis HP, S. hominis IMF12, Staphylococcus aureus SA113, S. aureus DPC 5247, S. aureus NCD1499, S. aureus RF122, S. aureus Newman, S. aureus 528 (MRSA), S. aureus 530 (MRSA), S. aureus 523 (MRSA), S. epidermidis IMF54, hVISA32652, hVISA32679, Streptococcus agalactiae ATCC13813, Streptococcus dysgalactiae 43078, and Streptococcus mutans, Vancomycin resistant Enterococcus VRE Ec520, VRE Ec295, VRE Ec533, VRE Ec725, VRE Ec538, Enterococcus faecium IMF91, Enterococcus durans 5133, Enterococcus durans IMF90, Propionibacterium acnes, Bacillus cereus IMF4 and Micrococcus luteus. Gram Negative: C. sakazakii DPC 6440, C. sakazakii DPC 6441, C. sakazakii DPC 6442, C. sakazakii DPC 6443, C. sakazakii DPC 6444, C. sakazakii DPC 6448, C. sakazakii DPC 6522, C. sakazakii DPC 6524, C. sakazakii DPC6440, C. sakazakii DPC6442, C. sakazakii DPC6446. |
| S29A | Gram Positive: L. lactis MG1363, L. lactis HP, S. aureus SA113, S. aureus DPC 5247, S. aureus NCD01499, S. aureus RF122, S. hominis IMF12, S. epidermidis IMF54, S. mutans, S. agalactiae ATCC13813, S. aureus 528 (MRSA), S. aureus 530 (MRSA), hVISA32652, hVISA32679, Enterococcus durans 5133, Bacillus cereus DPC 6088, Bacillus cereus IMF4, Bacillus firmus IMF68, Enterococcus faecium IMF91, Enterococcus durans IMF90, L. monocytogenes LO28 and L. monocyotgenes 10403s. Gram Negative: C. sakazakii DPC 6440, C. sakazakii DPC 6441, C. sakazakii DPC 6442, C. sakazakii DPC 6443, C. sakazakii DPC 6444, C. sakazakii DPC 6522, C. sakazakii DPC 6524, C. sakazakii DPC6440, C. sakazakii DPC6442, C. sakazakii DPC6446 |
| S29D | Gram Positive: L. lactis HP, S. aureus DPC 5247, S. aureus NCD01499, S. hominis IMF12, S. agalactiae ATCC13813, Streptococcus mutans, Streptococcus dysgalactiae 43078, S. aureus Newman, S. aureus 528 (MRSA), S. aureus 523 (MRSA), VRE Ec295, VRE Ec725, VRE Ec538, Lactococcus lactis MG1363, L. lactis HP, Propionibacterium acnes, Bacillus firmus IMF68, Enterococcus faecium IMF91, Enterococcus durans IMF90, and Micrococcus luteus. Gram Negative: C. sakazakii DPC6446. |

TABLE 2-continued

Nisin derivatives with enhanced bioactivity

| Strain | |
|---|---|
| S29E | Gram Positive: *L. lactis* HP, *S. aureus* DPC 5247, *S. aureus* NCD01499, *Streptococcus dysgalactiae* 43078, *S. mutans*, *S. aureus* Newman, hVISA32652 Ec295, VRE Ec533 *L. lactis* HP, *Enterococcus durans* 5133, *Enterococcus durans* IMF90, and *Propionibacterium acnes*. |
| | Gram Negative: *C. sakazakii* DPC 6442, *C. sakazakii* DPC 6443, *C. sakazakii* DPC 6448, *C. sakazakii* DPC6446. |
| S29R | Gram Positive: *Listeria monocytogenes* LO28, |
| | Gram Negative: *C. sakazakii* DPC6446. |
| Nisin Z Derivative | |
| S29G | *S. aureus* RF122, *L. lactis* HP |
| S29D | *L. lactis* HP |
| S29E | *L. lactis* HP |
| S29N | *L. lactis* HP |
| Nisin F Derivative | |
| S29A | *L. lactis* HP |
| S29E | *L. lactis* HP |
| S29V | *L. lactis* HP |
| S29N | *L. lactis* HP |
| Nisin Q Derivative | |
| S29A | *L. lactis* HP, *S. aureus* RF122 |
| S29D | *L. lactis* HP |
| S29E | *L. lactis* HP |
| S29P | *L. lactis* HP |

Advantageously, Nisin A S29G has been found to be more active against *Listeria monocytogenes* LO28, *L. monocytogenes* 10403s, *L. monocytogenes* EGDe ΔvirR and *L. monocytogenes* EGDe Δmprf *Lactococcus lactis* MG1363, *L. lactis* HP, *Bacillus cereus, Staphylococcus aureus* SA113, *S. aureus* DPC 5247, *S. aureus* NCD1499, *S. aureus* RF122, *S. aureus* Newman, *S. aureus* 528 (MRSA), *S. aureus* 530 (MRSA), *S. aureus* 523 (MRSA), *S. epidermidis* IMF54, hVISA32652, hVISA32679, *S. hominis* IMF12, *Streptococcus agalactiae* ATCC13813, *Streptococcus dysgalactiae* 43078, *Streptococcus mutans*, Vancomycin resistant *Enterococcus* VRE Ec520, VRE Ec295, VRE Ec533, VRE Ec725, VRE Ec538, *E. faecium* IMF91, *Enterococcus durans* 5133, *Enterococcus durans* IMF90, *Bacillus cereus* IMF4, *Propionibacterium acnes, Micrococcus luteus, Cronobacter sakazakii* DPC 6440, *C. sakazakii* DPC 6441, *C. sakazakii* DPC 6442, *C. sakazakii* DPC 6443, *C. sakazakii* DPC 6444, *C. sakazakii* DPC 6448, *C. sakazakii* DPC 6522, *C. sakazakii* DPC 6524, *C. sakazakii* DPC6440, *C. sakazakii* DPC6442, *C. sakazakii* DPC6446 than natural Nisin A.

Nisin A S29A is more active against *L. lactis* MG1363, *L. lactis* HP, *S. aureus* SA113, *S. aureus* DPC 5247, *S. aureus* NCD01499, *S. aureus* RF122, *S. hominis* IMF12, *S. epidermidis* IMF54, *S. mutans, S. agalactiae* ATCC13813, *S. aureus* 528 (MRSA), *S. aureus* 530 (MRSA), hVISA32652, hVISA32679, *Enterococcus durans* 5133, *Bacillus cereus* DPC 6088, *Bacillus cereus* IMF4, *Bacillus firmus* IMF68, *Enterococcus faecium* IMF91, *Enterococcus durans* IMF90, *L. monocytogenes* LO28, *L. monocyotgenes* 10403s, *C. sakazakii* DPC 6440, *C. sakazakii* DPC 6441, *C. sakazakii* DPC 6442, *C. sakazakii* DPC 6443, *C. sakazakii DPC* 6444, *C. sakazakii* DPC 6522, *C. sakazakii* DPC 6524, *C. sakazakii* DPC6440, *C. sakazakii* DPC6442, *C. sakazakii* DPC6446 than natural Nisin A.

Nisin A S29D is more active against *L. lactis* HP, *S. aureus* DPC 5247, *S. aureus* NCD01499, *S. agalactiae* ATCC13813, *Streptococcus mutans, Streptococcus dysgalactiae* 43078, *S. aureus* Newman, *S. aureus* 528 (MRSA), *S. aureus* 523 (MRSA), *S. hominis* IMF12, VRE Ec295, VRE Ec725, VRE Ec538 *Lactococcus lactis* MG1363, *L. lactis* HP, *Propionibacterium acnes, Bacillus cereus, Bacillus firmus* IMF68, *Enterococcus faecium* IMF91, *Enterococcus durans* IMF90, *Micrococcus luteus, C. sakazakii* DPC6446 than natural Nisin A.

Nisin A S29E is more active against *L. lactis* HP, *S. aureus* DPC 5247, *S. aureus* NCD01499, *Streptococcus* dysgalactiae 43078, *S. mutans, S. aureus* Newman, hVISA32652, Ec295, VRE Ec533, *Enterococcus durans* 5133, *Enterococcus durans* IMF90, *Propionibacterium acnes, C. sakazakii* DPC 6442, *C. sakazakii* DPC 6443, *C. sakazakii* DPC 6448, *C. sakazakii* DPC6446 than natural Nisin A.

Nisin A S29R is more active against *L. monocytogenes* LO28 and *C. sakazakii* DPC6440 than natural Nisin A.

Nisin Z S29G is more active against *S. aureus* RF122 and *L. lactis* HP than natural Nisin Z.

Nisin Z S29G is more active against *L. lactis* HP than natural Nisin Z.

Nisin Z S29D is more active against *L. lactis* HP than natural Nisin Z.

Nisin Z S29E is more active against *L. lactis* HP than natural Nisin Z.

Nisin Z S29N is more active against *L. lactis* HP than natural Nisin Z.

Nisin F S29A is more active against *L. lactis* HP than natural Nisin F.

Nisin F S29E is more active against *L. lactis* HP than natural Nisin F.

Nisin F S29V is more active against *L. lactis* HP than natural Nisin F.

Nisin F S29N is more active against *L. lactis* HP than natural Nisin F.

Nisin Q S29A is more active against *L. lactis* HP and *S. aureus* RF122 than natural Nisin Q.

Nisin Q S29D is more active against *L. lactis* HP than natural Nisin Q.

Nisin Q S29E is more active against *L. lactis* HP than natural Nisin Q.

Nisin Q S29P is more active against *L. lactis* HP than natural Nisin Q.

Use of the nisin Z Ser29Ala mutant against gram positive bacteria such as *Micrococcus flavus, Streptococcus pneumoniae* and *Staphylococcus epidermidis* is excluded from the scope of the present invention. This is particularly the case where bacteriostatic activity is desired. However, the Nisin Z Ser29Ala mutant may be advantageously used against gram-negative bacteria. Suitably, such gram-negative bacteria include: *Escherichia coli, Salmonella enteritidis, Pseudomonas aeruginosa, Campylobacter jejuni, Campylobacter coli, Hemophilus influenzae, Klebsiella pneumoniae, Legionella pneumophila, Proteus mirabilis, Enterobacter cloacae, Serratia marcescens, Helicobacter pylori, Salmonella typhi, Acinetobacter baumannii* and *Cronobacter sakazakii.*

In particular, Nisin Z Ser29Ala mutant may be used against gram-negative organisms are preferably *Cronobacter sakazakii.*

Suitably, Nisin Z Ser29Ala mutant may be used against the gram negative bacteria may be selected from the group consisting of *C. sakazakii* DPC 6440, *C. sakazakii* DPC 6441, *C. sakazakii* DPC 6442, *C. sakazakii* DPC 6443, *C. sakazakii* DPC 6444, *C. sakazakii* DPC 6448, *C. sakazakii* DPC 6522, *C. sakazakii* DPC 6524, *C. sakazakii* DPC6440, *C. sakazakii* DPC6442 and *C. sakazakii* DPC6446.

In a further aspect of the current invention, there is provided the use of a mutant derivative of Nisin or a Nisin variant, as a food or beverage additive, preservative or shelf life extender (the skilled person will appreciate that this is intended to mean that the mutation is found in any natural Nisin variant). Such additives may be in liquid form and/or tablet form. The derivatives of the invention may be incorporated directly, as part of an ingredient or via in situ production by a microorganisms, into liquids (including milk or beer), foods or related packaging either alone or in combination with of a large variety of other agents (or combined with high temp, high pressure, etc.).

In a further embodiment, there is provided a food additive comprising a mutant derivative of Nisin or a Nisin variant, as described herein.

According to a further embodiment of the invention still, there is provided for use of a mutant derivative of Nisin or a Nisin variant in the manufacture of a medicament for the treatment or prevention of disease caused by gram-positive and/or gram-negative pathogens.

Furthermore, the invention contemplates the use of a mutant Nisin or mutant Nisin variant producing strain for the treatment or prevention of disease.

Suitably, the disease may include, but is not limited to, bovine mastitis, oral infections including dental plaque and bad breath, gastric ulcers, CDAD (*Clostridum difficile* associated diarrhoea), acne, and bacterial infections generally.

The bacterial infections may be caused by gram-positive and/or gram-negative bacteria.

The mutant derivative of Nisin or a Nisin variant as described herein may also find use as spermicides, surfactants or preservatives.

For example, suitably, the Nisin derivatives of the current invention may be used as a preservative in cosmetics or in eye drops.

A further aspect of the current invention provides a pharmaceutical composition for use in the treatment and prevention of infections caused by gram-positive organisms and/or gram-negative organisms, wherein said composition comprises a mutant derivative of Nisin or a Nisin variant derivative of the invention. The pharmaceutical composition, comprising the mutant of any one of may be together with a pharmaceutically acceptable carrier or excipient.

A preferred embodiment of the current invention provides for a pharmaceutical composition for use in the treatment and prevention of infections caused by gram-negative organisms, wherein the composition comprises a Nisin derivative of the invention.

The pharmaceutical composition may include a carrier or excipient as appropriate.

The present invention also provides use of the Nisin and Nisin variant derivatives of the current invention (which have enhanced bioactivity), as a pharmaceutical composition, a disinfectant, or a food additive, together with carriers or excipients, as appropriate.

A particularly preferred use of the mutants of the invention are as food additives.

Other preferred uses include use of a natural Nisin variant comprising an amino acid substitution at amino acid position 29 in the amino acid sequence; or use of a mutant of a natural Nisin variant comprising an amino acid substitution at amino acid position 29 comprising at least one further amino acid substitution, preferably at the amino acid position 30 in the amino acid sequence, or use of mixtures thereof, wherein the Nisin derivative exhibits an antimicrobial activity compared to wild type Nisin, in cheese pasteurisation, as a compound to extend: shelf-life, increase safety and quality of food products in beverage production, in cosmetic preservation, as a spermicide, as a surfactant or as a disinfectant.

According to another embodiment of the present invention, there is provided a vector/plasmid comprising a sequence encoding a Nisin derivative as defined above. Suitably, the sequence may be an amino acid sequence or a nucleotide sequence.

The present invention further provides a host cell, for example, a bacterium host cell, with a vector encoding a Nisin derivative of the present invention. In a related aspect, the present invention also relates to a Nisin derivative or a host producing a Nisin derivative of the current invention.

In another aspect, the invention also provides a method of treating or preventing a disease comprising a Nisin derivative of the current invention, as described herein.

Suitably, the disease may be caused by gram-positive or negative pathogens, or mixtures of both. The disease may be selected from the group consisting of: bovine mastitis, dental plaque, gastric ulcers, CDAD (*Clostridum difficile* associated diarrhoea), acne and bacterial infections.

Table 3 provides the molecular weights of the Nisin A S29 derivatives as observed by mass spectrometry are listed. In the case of S29C, colony mass spec did not yield a detectable mass. This mutant was identified by sequence analysis of colonies producing little/no detectable zone of inhibition (Sep. 9, 2009). The molecular weights of some derivatives of the invention are as follows:—

TABLE 3

S29X derivatives identified in NisinA, NisinZ, NisinF and NisinQ backgrounds.

| Amino acid | NisinA-S29X | NisinZ-S29X | NisinF-S29X | NisinQ-S29X |
|---|---|---|---|---|
| N | 3379.66 | 3358.92 | 3341.45 | nd |
| Q | 3393.69 | 3372.41 | nd | 3367.38 |
| C | 3368.70 | nd | nd | nd |
| G | 3322.60 | 3300.64 | 3286.77 | 3299.07 |
| A | 3336.64 | 3314.55 | 3299.41 | 3311.85 |
| S | 3353.15 (WT) | 3331.63 (WT) | 3316.85 (WT) | 3327.50 (WT) |
| T | 3366.66 | 3344.91 | 3329.03 | 3342.64 |
| V | 3364.69 | 3343.08 | 3327.44 | 3340.10 |
| L | 3378.71 | 3356.42 | 3341.95 | 3353.85 |
| I | 3378.71 | 3356.06 | 3340.50 | 3353.85 |
| P | 3362.67 | 3341.27 | 3326.56 | 3338.64 |
| M | 3396.74 | 3374.82 | 3360.86 | nd |
| F | 3412.73 | 3390.79 | 3376.40 | nd |
| Y | 3428.73 | 3407.16 | 3394.39 | 3403.74 |
| W | 3451.76 | 3429.48 | 3415.04 | nd |
| D | 3380.64 | 3355.30 | 3343.60 | 3354.11 |
| E | 3394.67 | 3373.15 | 3357.93 | 3367.97 |
| R | 3421.74 | 3399.69 | 3385.13 | 3397.29 |
| H | 3402.69 | nd | 3364.28 | 3376.93 |
| K | 3393.72 | 3372.66 | nd | nd | nd—derivative not detected

In a related aspect, the invention further provides primers or probes to detect or amplify the substitutions or a Nisin derivative of the current invention.

The terms "Nisin Derivative" or "Nisin Variant" as used herein refer to a Nisin peptide or protein or natural variant thereof, with at least one amino acid mutation or substitution in the amino acid sequence.

The term "wild type Nisin" refers to a Nisin peptide or protein without an amino acid substitution or mutation at amino acid position 29.

Unless otherwise defined, all terms of scientific terminology used herein are intended to have the meanings commonly understood by those of skill in the art. In some cases, terms are defined herein for clarity and should not be intended to limit the scope of the invention in any way. It is to be understood that the following detailed description and accompanying figures, are exemplary and explanatory only and are intended to provide a further explanation of the present invention, as claimed and not to limit the scope of the invention in any way.

The current invention will now be described with reference to the following examples.

DETAILED DESCRIPTION OF THE INVENTION

Figure 1:
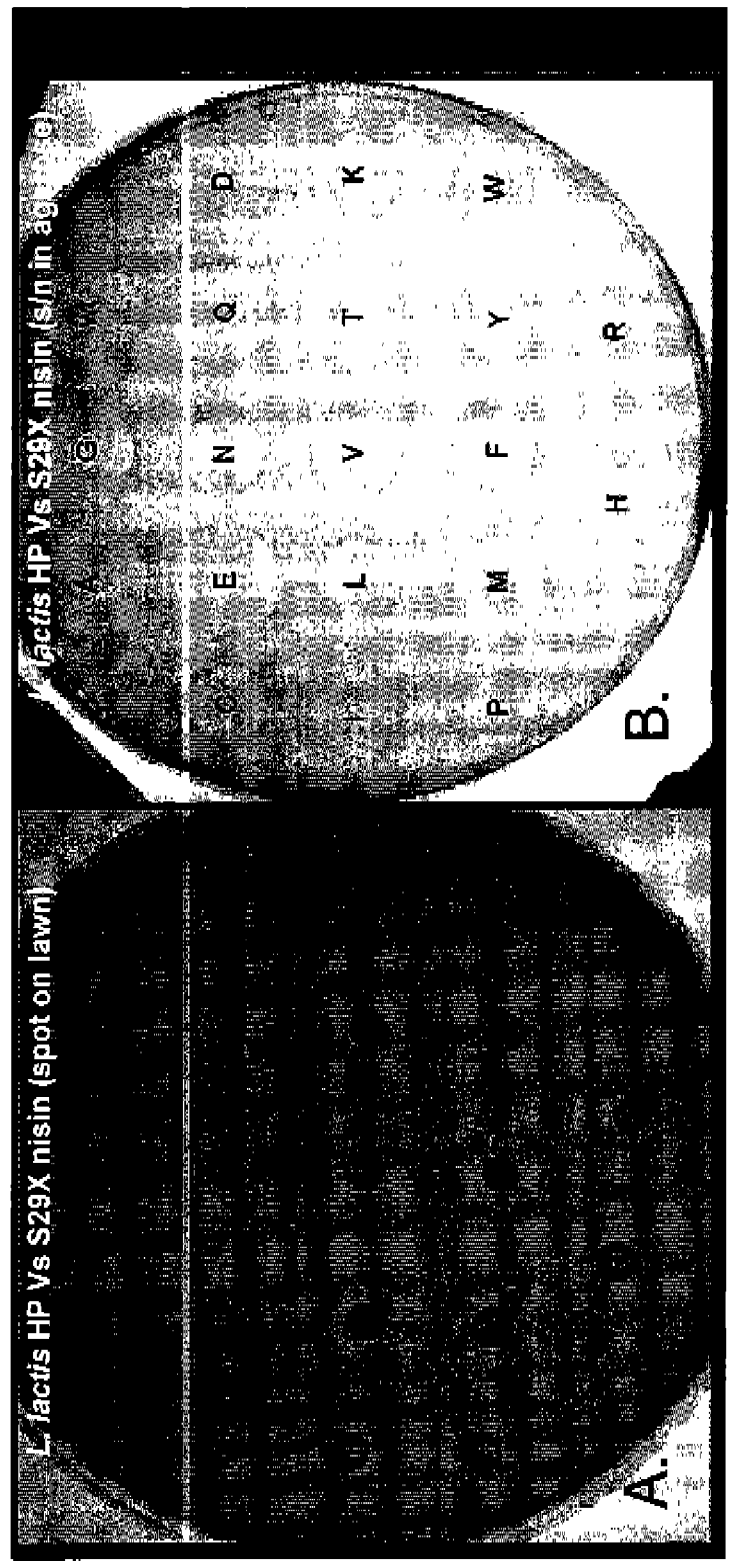
FIG. 1 illustrates a photograph of the results of an Agar-based deferred antagonism assay (spot on lawn) of Nisin A S29 derivatives (left) and agarose-based antagonism assays (supernatants) (right) against the indicator strain *Lactococcus lactis* HP.

Materials and Methods
Bacterial Strains and Growth Conditions

Bacterial strains and plasmids used in this study are listed in Table 4. *L. lactis* strains were grown in M17 broth supplemented with 0.5% glucose (GM17) or GM17 agar at 30° C. *E. coli* was grown in Luria-Bertani broth with vigorous shaking or agar at 37° C. *S. aureus* and *Micrococcus luteus* strains were grown in Mueller-Hinton (MH) broth (Oxoid) or MH agar at 37° C., streptococci and *Bacillus* strains were grown in Tryptic soy broth (TSB) or TSB agar at 37° C., *Listeria* strains were grown in Brain Heart Infusion (BHI) or BHI agar at 37° C. Vancomycin resistant enterococci (VRE) were cultured in cation-adjusted Mueller-Hinton broth in accordance with the CLSI microbroth method at 37° C. without aeration. Antibiotics were used where indicated at the following concentrations: Chloramphenicol at 10 and 20 μg ml$^{-1}$, respectively for *L. lactis* and *E. coli*. Tetracycline was used at 10 μg ml$^{-1}$ for *L. lactis* and *E. coli* and ampicillin was used at 50 μg ml for *E. coli*.

TABLE 4

Bacterial strains and plasmids utilised in the current study.

| Strain/plasmids | Relevant characteristics | Reference |
|---|---|---|
| Strains | | |
| *L. lactis* NZ9700 | Wild type Nisin producer | (Kuipers et al. 1993; Kuipers et al. 1998) |
| *L. lactis* NZ9800 | *L. lactis* NZ9700 ΔnisA | (Kuipers et al. 1993; Kuipers et al. 1998) |

TABLE 4-continued

Bacterial strains and plasmids utilised in the current study.

| Strain/plasmids | Relevant characteristics | Reference |
|---|---|---|
| *L. lactis* NZ9800 pPTPL | *L. lactis* NZ9800 harbouring pPTPL | (Field et al., 2008) |
| *L. lactis* NZ9800 pDF05 | *L. lactis* NZ9800 harbouring pDF05 | (Field et al., 2008) |
| *E. coli* MC1000 | *E. coli* host for pPTPL | (O'Driscoll et al., 2004) |
| *E. coli* MC1000 pPTPL | *E. coli* harbouring pPTPL | (O'Driscoll et al., 2004) |
| *E. coli* Top10 | Intermediate cloning host | Stratagene |
| Indicator organisms | | |
| *Strep. agalactiae* ATCC13813 | Nisin sensitive indicator | American Type Culture |
| *Strep. mutans* | Nisin sensitive indicator | Collection |
| *S. dysgalactiae* ATCC43078 | Nisin sensitive indicator | UCC Culture Collection |
| *S. aureus* NCDO 1499 | Nisin sensitive indicator | American Type Culture |
| *S. aureus* SA113 | Nisin sensitive indicator | Collection |
| *S. aureus* RF122 | Nisin sensitive indicator | DPC Collection |
| *S. aureus* Newman | Nisin sensitive indicator | UCC Culture Collection |
| *S. aureus* DPC5247 | Nisin sensitive indicator | UCC Culture Collection |
| *S. aureus* ST528 (MRSA) | Nisin sensitive indicator | UCC Culture Collection |
| *S. aureus* ST530 (MRSA) | Nisin sensitive indicator | DPC Collection |
| *S. aureus* ST523 (MRSA) | Nisin sensitive indicator | BSAC |
| hVISA32679 | Nisin sensitive indicator | BSAC |
| hVISA32652 | Nisin sensitive indicator | BSAC |
| VRE Ec538 | Nisin sensitive indicator | BSAC |
| VRE Ec295 | Nisin sensitive indicator | BSAC |
| VRE Ec725 | Nisin sensitive indicator | BSAC |
| VRE Ec533 | Nisin sensitive indicator | BSAC |
| VRE Ec520 | Nisin sensitive indicator | BSAC |
| *L. monocytogenes* 10403S | Nisin sensitive indicator | BSAC |
| *L. monocytogenes* LO28 | Nisin sensitive indicator | BSAC |
| *L. monocytogenes* EGDeΔvirR | Nisin sensitive indicator | UCC Culture Collection |
| *L. monocytogenes* EGDeΔmprf | Nisin sensitive indicator | UCC Culture Collection |
| *L. lactis* ssp *cremoris* HP | Nisin sensitive indicator | UCC Culture Collection |
| *Lactococcus lactis* MG1363 | Nisin sensitive indicator | UCC Culture Collection |
| *Micrococcus luteus* | Nisin sensitive indicator | UCC Culture Collection |
| *Bacillus cereus* | Nisin sensitive indicator | UCC Culture Collection |
| *Propionibacterium acnes* | Nisin sensitive indicator | UCC Culture Collection |
| *B. cereus* DPC 6088 | Nisin sensitive indicator | UCC Culture Collection |
| *B. cereus* DPC 6089 | Nisin sensitive indicator | DPC Collection |
| *E. durans* 5133 | Nisin sensitive indicator | DPC Collection |
| *Bacillus cereus* IMF4 | Infant milk formula (IMF isolate) | DPC Collection |
| *Staphylococcus hominis* IMF12 | IMF isolate | UCC Culture Collection |
| *Staphylococcus epidermidis* IMF54 | IMF isolate | UCC Culture Collection |
| *Bacillus firmus* IMF68 | IMF isolate | UCC Culture Collection |
| *Enterococcus durans* IMF90 | IMF isolate | UCC Culture Collection |
| *Enterococcus faecium* IMF91 | IMF isolate | UCC Culture Collection |
| *C. sakazakii* DPC6448 | Indicator strain | UCC Culture Collection |
| *C. sakazakii* DPC6445 | Indicator strain | DPC Collection |
| *C. sakazakii* DPC6444 | Indicator strain | DPC Collection |
| *C. sakazakii* DPC6443 | Indicator strain | DPC Collection |
| *C. sakazakii* DPC6442 | Indicator strain | DPC Collection |
| *C. sakazakii* DPC6441 | Indicator strain | DPC Collection |
| *C. sakazakii* DPC6522 | Indicator strain | DPC Collection |
| *C. sakazakii* DPC6524 | Indicator strain | DPC Collection |
| *C. sakazakii* DPC6440 | Indicator strain | DPC Collection |
| *C. sakazakii* DPC6442 | Indicator strain | DPC Collection |

TABLE 4-continued

Bacterial strains and plasmids utilised in the current study.

| Strain/plasmids | Relevant characteristics | Reference |
|---|---|---|
| C. sakazakii DPC6446 | Indicator strain | DPC Collection |
|  | Indicator strain | DPC Collection |
| Plasmids |  |  |
| pCI372 | Cm$^R$; High-copy cloning vector | (Hayes et al., 1990) |
| pDF05 | pCI372 with nisA under its ownpromoter | This study |
| pPTPL | Tet$^R$; lacZ; Low-copy cloning vector | (O'Driscoll et al., 2004) |
| pDF03 |  | (Field et al., 2008) |
| pUC19 |  |  |
| pDF04 | pPTPL with nisA under its own promoter AMP$^R$; lacZ; High-copy cloning vector. pUC19 with nisA under its own promoter | (Field et al., 2008) |

Random Mutagenesis

DNA obtained from L. lactis NZ9700 (Hoffmann et al., 2004) was used as template for the amplification of a 372 bp fragment encompassing the nisA gene with KOD polymerase (Novagen) using the primers oDF101 and oDF102. PCR amplicons were purified using the QIAquick PCR purification kit (QIAGEN Inc.), digested with BglII and XbaI (Roche) and cloned into similarly digested and Shrimp Alkaline Phosphatase (SAP; Roche) treated pPTPL. Following introduction into E. coli MC1000, plasmid was isolated from one clone and was sequenced (MWG Biotech, Germany) using the primer TETK P1 to ensure its integrity. The introduction of this plasmid, pDF03, into competent L. lactis NZ9800 successfully reinstated Nisin activity. To provide sufficient quantities of template DNA for error-prone PCR (ep-PCR), nisA was reamplified using pDF03 as template with KOD polymerase using the primers oDF101 and oDF103, digested with Xba1 and EcoR1 and cloned into similarly digested pUC19. Following introduction into E. coli Top 10 (Invitrogen), plasmid was isolated from one clone and was sequenced (MWG Biotech, Germany) using the primers M13FOR and M13REV to ensure its integrity. This plasmid, pDF04 was isolated from 100 ml overnight culture using the Maxi-prep plasmid kit (QIAGEN Inc.) to a concentration of approx 1,100 ng/μl. pDF04 was used as template for the Genemorph II random mutagenesis kit (Stratagene) according to manufacturer's guidelines. To introduce an average of one base change in the 372 bp cloned fragment, amplification was performed in a 50 μl reaction containing approximately 500 ng of target DNA (pDF04), 2.5 units Mutazyme DNA polymerase, 1 mM dNTPs and 200 ng each of primers oDF101 and oDF102. The reaction was preheated at 96° C. for 1 min, and then incubated for 22 cycles at 96° C. for 1 min, 52° C. for 1 min and 72° C. for 1 min, and then finished by incubating at 72° C. for 10 min. Amplified products were purified by gel extraction using the Qiaquick gel extraction kit (QIAGEN Inc), and reamplified with KOD polymerase before being digested with BglII and XbaI (Roche), ligated with similarly digested and SAP treated pPTPL and introduced into E. coli MC1000. To determine if the correct rate of mutation had been achieved recombinant plasmid DNA was isolated from selected clones using the QIAprep Spin miniprep kit (QIAGEN Inc) and sequenced (MWG Biotech). Transformants were pooled and stored in 80% glycerol at −20° C. Plasmid DNA isolated from the mutant bank was used to transform L. lactis NZ9800. Transformants (approx. 8000) were isolated from Q trays using the Genetix QPIX II-XT colony-picking robot and inoculated into 96 well plates containing GM17 freezing buffer, incubated overnight and subsequently stored at −20° C.

Saturation Mutagenesis

To generate a template for mutagenesis, the 372 base pair fragment encompassing the nisA gene was amplified with KOD polymerase using the primers oDF102 and oDF103, was digested and subsequently cloned into pCI372. Following introduction into E. coli Top 10 cells, plasmid was isolated from one clone and was sequenced (MWG Biotech, Germany) using the primer pCI372REV to ensure its integrity. Saturation mutagenesis of the serine codon at position 29 of nisA was carried out with pDF05 (pCI372-nisA) as template and using oligonucleotides NisS29deg FOR 5' Pho-TGTCATTGTNNKATTCACGTAAGCAAATAA 3' and NisS29deg REV 5' TACGTGAATMNNACAATGACAAGT-TGCTGTTTTCATGTT 3' containing an NNK codon in place of each native codon. PCR amplification was performed in a 50 μl reaction containing approximately 0.5 ng of target DNA (pDF05), 1 unit Phusion High-Fidelity DNA polymerase (Finnzymes, Finland), 1 mM dNTPs and 500 ng each of the appropriate forward and reverse oligonucleotide. The reaction was preheated at 98° C. for 2 mins, and then incubated for 29 cycles at 98° C. for 30 secs, 55° C. for 15 secs and 72° C. for 3 mins 30 secs, and then finished by incubating at 72° C. for 3 mins 30 secs. Amplified products were treated with Dpn1 (Stratagene) for 60 mins at 37° C. to digest template DNA and purified using the QIAquick PCR purification kit. Following transformation of E. coli Top 10 cells plasmid DNA was isolated and sequenced to verify that mutagenesis had taken place. The purified products were subsequently introduced by electroporation into the strain NZ9800 which has all the genes necessary for Nisin production. Approximately 180 transformants were chosen at random and inoculated into 96 well plates containing GM17 chloramphenicol, incubated overnight and stored at −20° C. after addition of 80% glycerol. A similar strategy was employed to carry out site saturation mutagenesis of residue 29 in Nisin Z, Nisin F and Nisin Q as well as the simultaneous saturation of residues 29 and 30 in Nisin A.

Nisin Purification

L. lactis NZ9700 (Nisin A producer) or the mutant Nisin strain of interest was subcultured twice in GM17 broth at 1% at 30° C. before use. Two liters of modified TY broth were inoculated with the culture at 0.5% and incubated at 30° C. overnight. The culture was centrifuged at 7,000 rpm for 15 minutes. The cell pellet was resuspended in 300 mls of 70% isopropanol 0.1% TFA and stirred at room temperature for approximately 3 h. The cell debris was removed by centrifugation at 7,000 rpm for 15 minutes and the supernatant retained. The isopropanol was evaporated using a rotary evaporator (Buchi) and the sample pH adjusted to 4 before applying to a 10 g (60 ml) Varian C-18 Bond Elut Column (Varian, Harbor City, Calif.) pre-equilibrated with methanol and water. The columns were washed with 100 mls of 20% ethanol and the inhibitory activity was eluted in 100 mls of 70% IPA 0.1% TFA. 15 ml aliquots were concentrated to 2 ml through the removal of propan-2-ol by rotary evaporation. 1.5 ml aliquots were applied to a Phenomenex (Phenomenex, Cheshire, UK) C12 reverse phase (RP)-HPLC column (Jupiter 4u proteo 90 Å, 250×10.0 mm, 4 μm) previously equilibrated with 25% propan-2-ol, 0.1% trifluoroacetic acid TFA. The column was subsequently developed in a gradient of 30% propan-2-ol containing 0.1% TFA to 60% propan-2-ol containing 0.1% TFA from 10 to 45 minutes at a flow rate of 1.2 ml min$^{-1}$.

Mass Spectrometry

For Colony Mass Spectrometry (CMS) bacterial colonies were collected with sterile plastic loops and mixed with 50 μl of 70% isopropanol adjusted to pH 2 with HCl. The suspension was vortexed, the cells centrifuged in a benchtop centrifuge at 14,000 r.p.m. for 2 mins, and the supernatant was removed for analysis. Mass Spectrometry in all cases was performed with an Axima CFR plus MALDI TOF mass spectrometer (Shimadzu Biotech, Manchester, UK). A 0.5 μl aliquot of matrix solution (alpha-cyano-4-hydroxy cinnamic acid (CHCA), 10 mg ml$^{-1}$ in 50% acetonitrile-0.1% (v/v) trifluoroacetic acid) was placed onto the target and left for 1-2 mins before being removed. The residual solution was then air-dried and the sample solution (resuspended lyophilised powder or CMS supernatant) was positioned onto the pre-coated sample spot. Matrix solution (0.5 μl) was added to the sample and allowed to air-dry. The sample was subsequently analysed in positive-ion reflectron mode.

Bioassays for Antimicrobial Activity

Deferred antagonism assays were performed by replicating strains on GM17 agar plates and allowing them to grow overnight before overlaying with either GM17/BHI/TSB-YE/MH agar (0.75% w/v agar) seeded with the appropriate indicator strain. For higher throughput screening of the S29X bank, deferred antagonism assays were performed by replicating strains using a 96 pin replicator (Boekel) or spotting 5 μl of a fresh overnight culture on GM17 agar plates and allowing them to grow overnight. Following overnight growth the strains were subjected to UV radiation for 30 minutes prior to overlaying with either GM17/BHI/TS/MH agar (0.75% w/v agar) seeded with the appropriate indicator Minimum Inhibitory Concentration Assays Minimum inhibitory concentration determinations were carried out in triplicate in 96 well microtitre plates. 96 well microtitre plates were pre-treated with bovine serum albumin (BSA) prior to addition of the peptides. Briefly, to each well of the microtitre plate 200 μL of phosphate buffered saline (PBS) containing 1% (w/v) bovine serum albumin (PBS/BSA) was added and incubated at 37° C. for 30 min. The wells were washed with 200 μL PBS and allowed to dry. Target strains were grown overnight in the appropriate conditions and medium, subcultured into fresh broth and allowed to grow to an OD$_{600}$ of ~0.5, diluted to a final concentration of $10^5$ cfu ml$^{-1}$ in a volume of 0.2 ml. Wild type Nisin and Nisin mutant peptides were adjusted to a 5 μM (hVISA), 2.5 μM (MRSA), 7.5 μM (L. monocytogenes 10403S) or 500 nM (L. lactis strains) starting concentration and 2-fold serial dilutions of each peptide were added to the target strain. After incubation for 16 h at 37° C. the MIC was read as the lowest peptide concentration causing inhibition of visible growth.

Results

Creation and Screening of a Bank of Nisin A Derivatives

Screening of the Nisin mutants for enhanced bioactivity uses deferred antagonism assays which are performed by replicating strains on GM17 agar plates and allowing them to grow overnight before overlaying with either GM17/BHI/TSB-YE/MH agar (0.75% w/v agar) seeded with the appropriate indicator strain. The procedure is as follows:

A DNA fragment containing the nisA gene and its native P$_{nis}$ promoter was amplified, and cloned into pPTPL (a reporter vector with a promoterless lacZ) to generate pDF03. This was subsequently introduced into L. lactis NZ9800. NZ9800 is derivative of a Nisin-producing strain, L. lactis NZ9700, from which the nisA gene has been deleted (Table 3). The heterologous expression of nisA from pDF03 successfully restored Nisin production to wildtype levels, confirming that this complementation system is suitable for expressing randomly mutagenized nisA genes. A second plasmid, pDF04 (pUC19-nisA), was used as a template for the generation of randomly mutated nisA fragments via mutazyme II PCR amplification (using conditions designed to achieve one nucleotide change on average per copy of nisA). These fragments were cloned into pPTPL and ultimately introduced into L. lactis NZ9800 resulting in a bank consisting of approximately 8000 potential variants. Screening of the bank was undertaken by way of deferred antagonism assays using two indicator strains S. aureus SA113 and L. monocytogenes LO28. One mutant colony tested exhibited an increased bioactivity against the two indicator strains. The exceptional strain exhibited an enhanced bioactivity (approx. 50% increase in zone size compared to the corresponding positive control) against S. aureus SA113 and L. monocytogenes LO28. Further testing of the mutant reveals enhanced bioactivity against Lactococcus lactis spp cremoris HP, S. aureus NCDO 1499 and S. aureus DPC5247.

Sequencing

DNA sequencing of the corresponding nisA gene revealed an alteration predicted to result in a change in residue 29 from a serine to glycine.

Site-Directed Mutagenesis

To determine if other Nisin A mutant derivatives that have been altered at amino acid 29 possess enhanced antimicrobial activity, site saturation mutagenesis of position 29 was carried out to generate a collection of such derivatives. A bank of approx 180 Nisin A S29X mutants was created.

The bank of 180 producers was screened against Lactococcus lactis HP and S. aureus DPC5247 and against S. agalactiae ATCC 13813 and S. aureus NCD01499 and a number of producers were found to produce zones of enhanced size relative to an unaltered control.

16 S29X mutants with enhanced activity were sent for mass spectrometric analysis which revealed the presence of 9 candidates producing a peptide of mass consistent with that of S29G as well as other peptides with masses of 3381, 3395, 3335 respectively. Sequencing of the corresponding genes confirmed that these masses correspond to S29G, as well as S29D (3381), S29E (3395) and S29A (3336).

Mass Spectrometry

Mass spectrometric analysis of 48 of the Nisin A mutants established that the residue at position 29 has been randomly altered as masses consistent with the following amino acid substitutions were observed: S29G, S29A, S29D, S29E, S29R, S29V, S29P, S29W, S29T, S29N, S291/L, S290, S29F, S29W. S29D, S29E, S29R, S29H, S29K.

The molecular weights of the Nisin A S29 derivatives as observed by mass spectrometry are listed in Table 5. In the case of S29C, colony mass spec did not yield a detectable mass. This mutant was identified by sequence analysis of colonies producing little/no detectable zone of inhibition.

TABLE 5

Molecular weights of the Nisin A derivatives of the current invention.

| Amino acid | S29Predicted | Actual |
|---|---|---|
| N | 3379.66 | 3379.05 |
| Q | 3393.69 | 3394.04 |
| C | 3368.70 | Not detected (sequenced) |
| G | 3322.60 | 3322.97 |
| A | 3336.64 | 3336.67 |
| S | WT | 3352.63 |
| T | 3366.66 | 3366.75 |
| V | 3364.69 | 3364.81 |
| L | 3378.71 | 3379.33 |

TABLE 5-continued

Molecular weights of the Nisin A derivatives of the current invention.

| Amino acid | S29Predicted | Actual |
|---|---|---|
| I | 3378.71 | 3378.60 |
| P | 3362.67 | 3362.73 |
| M | 3396.74 | 3396.19 |
| F | 3412.73 | 3412.94 |
| Y | 3428.73 | 3429.17 |
| W | 3451.76 | 3451.61 |
| D | 3380.64 | 3381.32 |
| E | 3394.67 | 3395.56 |
| R | 3421.74 | 3421.93 |
| H | 3402.69 | 3404.81 |
| K | 3393.72 | 3394.16 |

Antimicrobial Activity of Nisin A Derivatives as Assessed by Deferred Antagonism Assays A collection of Nisin producers, in which the Nisin peptide encoding gene nisA has been randomly altered, were subjected to a screening study to identify Nisin derivatives with enhanced antimicrobial activity.

Nisin A S29G exhibits enhanced bioactivity, compared to a corresponding Nisin A producing control against a number of different strains. This was determined by deferred antagonism assays.

S29G is more active against *Listeria monocytogenes* L028, *L. monocyotgenes* 10403s, *L. monocyotgenes* EGDe ΔvirR and *L. monocytogenes* EGDe Δmprf (the latter two being mutants of *L. monocytoenes* EGDe which exhibit an altered sensitivity to lantibiotics), *Lactococcus lactis* MG1363, *L. lactis* HP, *Bacillus cereus*, *Staphylococcus aureus* SA113, *S. aureus* DPC 5247, *S. aureus* NCD1499, *S. aureus* RF122, *S. aureus* Newman, *S. aureus* 528 (MRSA), *S. aureus* 530 (MRSA), *S. aureus* 523 (MRSA), hVISA32652, hVISA32679, *S. agalactiae* ATCC13813, *Streptococcus dysgalactiae* 43078, and *Streptococcus mutans*, Vancomycin resistant *Eneterococcus* VRE Ec520, VRE Ec295, VRE Ec533, VRE Ec725, VRE Ec538, *Propionibacterium acnes*, and *Micrococcus luteus* compared to Nisin A.

Nisin A S29A is more active against *L. lactis* MG1363, *L. lactis* HP, *S. aureus* SA113, *S. aureus* DPC 5247, *S. aureus* NCD01499, *S. mutans*, *S. agalactiae* ATCC13813, *S. aureus* 528 (MRSA), *S. aureus* 530 (MRSA), hVISA32652, hVISA32679 and *L. monocyotgenes* 10403s compared to Nisin A.

Nisin A S29D is more active against *L. lactis* HP, *S. aureus* DPC 5247, *S. aureus* NCD01499, *S. agalactiae* ATCC13813, *Streptococcus mutans*, *Streptococcus dysgalactiae* 43078, *S. aureus* Newman, *S. aureus* 528 (MRSA), *S. aureus* 523 (MRSA), VRE Ec295, VRE Ec725, VRE Ec538 *Lactococcus lactis* MG1363, *L. lactis* HP, *Propionibacterium acnes*, *Bacillus cereus* and *Micrococcus luteus* compared to Nisin A.

Nisin A S29E are more active against *L. lactis* HP, *S. aureus* DPC 5247, *S. aureus* NCD01499, *Streptococcus* dysgalactiae 43078, *S. aureus* Newman, hVISA32652, Ec295, VRE Ec533 *L. lactis* HP, *Propionibacterium acnes* and *Bacillus cereus* compared to Nisin A.

Broth-based MIC assays with purified peptides the S29G peptide possesses enhanced activity against *St. aureus* 528 (MRSA), *St. aureus* 530 (MRSA), hVISA 32679, *L. lactis* HP, *L. lactis* MG1363 and *L. monocytogenes* 10403S compared to Nisin A.

The S29A peptide possesses enhanced activity against *St. aureus* 528 (MRSA), *St. aureus* 530 (MRSA), hVISA 32679, *L. lactis* HP, *L. lactis* MG1363 and *L. monocytogenes* 10403S compared to Nisin A.

The S29D peptide possesses enhanced activity against *St. aureus* 528 (MRSA), *L. lactis* HP and *L. lactis* MG1363 compared to Nisin A.

The S29E peptide possesses enhanced activity against *L. lactis* HP.

Minimum Inhibitory Concentration Assay

To assess if enhanced activity could be attributed to enhanced specific activity, broth-based minimum inhibitory concentration assays with purified peptides were carried out against selected strains. Results are given in micromolar values. Instances where antimicrobial activity is increased are indicated by bold text.

| STRAIN | NisinA | S29G | S29A | S29D | S29E |
|---|---|---|---|---|---|
| ST 528[a] | 0.156 | 0.078 | 0.078 | 0.078 | 0.156 |
| ST 530[a] | 0.156 | 0.078 | 0.078 | 0.156 | 0.156 |
| hVISA 32679[b] | 1.25 | 0.625 | 0.625 | 1.25 | 1.25 |
| L. lactis HP | 0.062 | 0.031 | 0.015 | 0.015 | 0.015 |
| L. lactis 1363 | 0.250 | 0.125 | 0.062 | 0.125 | 0.250 |
| L. mono 10403S | 3.75 | 1.875 | 1.875 | 3.75 | 3.75 |

[a]Methicillin resistant *S. aureus*.
[b]heterogenous Vancomycin insensitive *S. aureus*

Agarose-Based Diffusion Assays to Detect Bioactivity

A modified agarose-based assay has been developed and has been found to be more sensitive when assessing bacteriocin activity from the supernatant of producing strains. The Nisin A S29 derivatives were retested using this assay (See FIG. 1).

The modified agarose-based assay was performed against 2 indicator strains, *L. lactis* spp *cremoris* HP (Table. 6) and *Listeria monocytogenes* LO28 (Table. 7).

TABLE 6

Agarose-based diffusion assays of Nisin A S29 supernatants Vs *L. lactis* HP.

| Amino acid (S29X) | L. lactis HP (a) | L. lactis HP (b) | L. lactis HP (c) | Average a + b + c |
|---|---|---|---|---|
| wt | 15.4 | 15.4 | 15.0 | 15.26 |
| G | 15.5 | 15.9 | 14.8 | <u>15.40</u> |
| A | 16.3 | 16.9 | 16.7 | <u>16.63</u> |
| D | 19.8 | 21.3 | 19.9 | <u>20.33</u> |
| Q | 15.3 | 15.2 | 15.4 | 15.30 |
| N | 12.9 | 13.5 | 11.5 | 12.63 |
| E | 18.7 | 19.0 | 18.3 | <u>18.66</u> |
| C | 10.9 | 11.3 | 9.4 | 10.53 |
| K | 8.9 | 10.9 | 9.8 | 9.86 |
| T | 11.0 | 12.9 | 12.4 | 12.1 |
| V | 11.7 | 12.0 | 11.2 | 11.63 |
| L | 12.6 | 13.5 | 12.2 | 12.76 |
| I | 9.2 | 11.3 | 9.2 | 9.9 |
| W | 11.6 | 13.5 | 11.2 | 12.1 |
| Y | 10.0 | 11.3 | 10.7 | 10.66 |
| F | 10.6 | 12.2 | 10.2 | 11.0 |
| M | 13.2 | 14.5 | 13.0 | 13.56 |
| P | 13.3 | 14.8 | 12.9 | 13.66 |
| R | 10.4 | 11.5 | 11.2 | 11.03 |
| H | 11.2 | 10.7 | 10.9 | 10.93 |

Measurement of inhibitory zone in mm

The results against *L. lactis* HP confirmed the previously identified enhanced Nisin A mutants S29G, S29A, S29D and S29E (highlighted above in bold underline). The results against *L. monocytogenes* LO28 established that just one of the 4 lead candidates, S29A, exhibited an enhanced phenotype against this target. Surprisingly, a derivative previously thought to be reduced in activity, Nisin A S29R (approx 50% reduced activity against HP), displayed an enhanced effect against *L. monocytogenes* LO28 (Table. 7). This result was confirmed in growth assays with serial dilutions of each S29 supernatant against *L. monocytogenes* LO28. (Data not shown)

TABLE 7

Agarose-based diffusion assays of selected Nisin A S29 supernatants Vs *L. monocytogenes* LO28.

| S29 | LO28a | LO28b | Avg |
|---|---|---|---|
| wt | 11.4 | 11.1 | 11.25 |
| G | 10.1 | 9.6 | 9.85 |
| A | 12.0 | 12.5 | 12.25 |
| E | 10.5 | 10.8 | 10.65 |
| D | 9.2 | 9.0 | 9.10 |
| R | 11.2 | 11.5 | 11.35 |

On the basis of the enhanced activity of Nisin A S29R against *L. monocytogenes* LO28, this peptide was selected to be included in further studies using purified peptides and MIC determination (Table. 8). It was decided to include the Nisin A M21V enhanced Nisin A derivative (also known as Nisin V) as a control. This peptide has previously been shown to display a two-fold increase in activity compared to wild-type against all strains tested in MIC assays. These studies confirmed the enhanced activity of Nisin A S29A and Nisin A S29R against *L. monocytogenes* LO28.

TABLE 8

Minimum Inhibitory concentrations of purified Nisin A S29 derivatives against *L. monocytogenes* LO28

| Wt Nisin mg l$^{-1}$ (μM) | M21V mg l$^{-1}$ (μM) | S29G mg l$^{-1}$ (μM) | S29A mg l$^{-1}$ (μM) | S29E mg l$^{-1}$ (μM) | S29D mg l$^{-1}$ (μM) | S29R mg l$^{-1}$ (μM) |
|---|---|---|---|---|---|---|
| 6.28 (1.875) | 3.14 (0.937) | 6.28 (1.875) | 3.14 (0.937) | 6.28 (1.875) | 12.56 (3.75) | 3.14 (0.937) |

Minimum Inhibitory Concentration Assay

The sensitivity of a greater variety of target strains to the lead Nisin A S29 derivatives, including in some instances S29R, was assessed using the MIC approach. Results (Table. 8) are given in micromolar values. Instances where antimicrobial activity is increased are indicated by bold text.

TABLE 8

Minimum inhibitory activity (micromolar values) of Nisin A S29 derivatives against a selection of strains

| STRAIN | NisinA | S29G | S29A | S29D | S29E | S29R |
|---|---|---|---|---|---|---|
| ST 528[a] | 0.156 | 0.078 | 0.078 | 0.078 | 0.156 | Nd |
| ST 530[a] | 0.156 | 0.078 | 0.078 | 0.156 | 0.156 | Nd |
| hVISA 32679[b] | 1.25 | 0.625 | 0.625 | 1.25 | 1.25 | Nd |
| *L. lactis* HP | 0.062 | 0.031 | 0.015 | 0.015 | 0.015 | 0.125 |
| *L. lactis* MG1363 | 0.250 | 0.125 | 0.062 | 0.125 | 0.250 | Nd |
| *L. mono* 10403S | 3.75 | 1.875 | 1.875 | 3.75 | 3.75 | Nd |
| *L. mono* LO28 | 1.875 | 1.875 | 0.937 | 3.75 | 1.875 | 0.937 |
| *S. aureus* RF122 | 0.312 | 0.156 | 0.156 | 1.25 | 0.625 | Nd |
| *S. mutans* | 2.5 | 2.5 | 1.25 | 5.0 | 1.25 | 5.0 |
| *B. cereus* DPC 6088 | 1.25 | 1.25 | 0.612 | 5.0 | 1.25 | 2.5 |
| *B. cereus* DPC 6089 | 2.5 | 1.25 | 1.25 | 2.5 | 1.25 | 2.5 |
| *E. durans* 5133 | 0.156 | 0.078 | 0.039 | 0.156 | 0.156 | 0.156 |

[a]Methicillin resistant *S. aureus*.
[b]heterogenous Vancomycin insensitive *S. aureus*.
nd = not determined Growth Curve Analysis The adoption of a modified growth assay (peptides are incubated with strains in sodium phosphate buffer for 3 hours prior to spectrophotometer analysis) provided a more sensitive means of assessing the antimicrobial effect of peptides on some bacterial strains.

A Gram negative strain *Cronobacter sakazakii* DPC 6440 was used as indicator in growth assays with wild-type peptide and the lead Nisin derivatives S29G, S29A, S29E, and S29D. The derivatives S29D and S29E displayed equal or less activity respectively than the wild-type peptide (data not shown), while S29G and S29A completely inhibited the growth of *C. sakazakii*. Triplicate plate counts taken at 24 hours revealed $1 \times 10^9$ *C. sakazakii* for the wild-type but no detectable cell numbers for either S29G and S29A (FIG. 2).

This is a significant break-through as Nisin, and indeed lantibiotics in general, are not noted for their activity against Gram negative bacteria (NB. Existing Nisin variants of note such as M21V [Nisin V] did not exhibit this potent anti-*C. sakazakii* activity).

Figure 2:
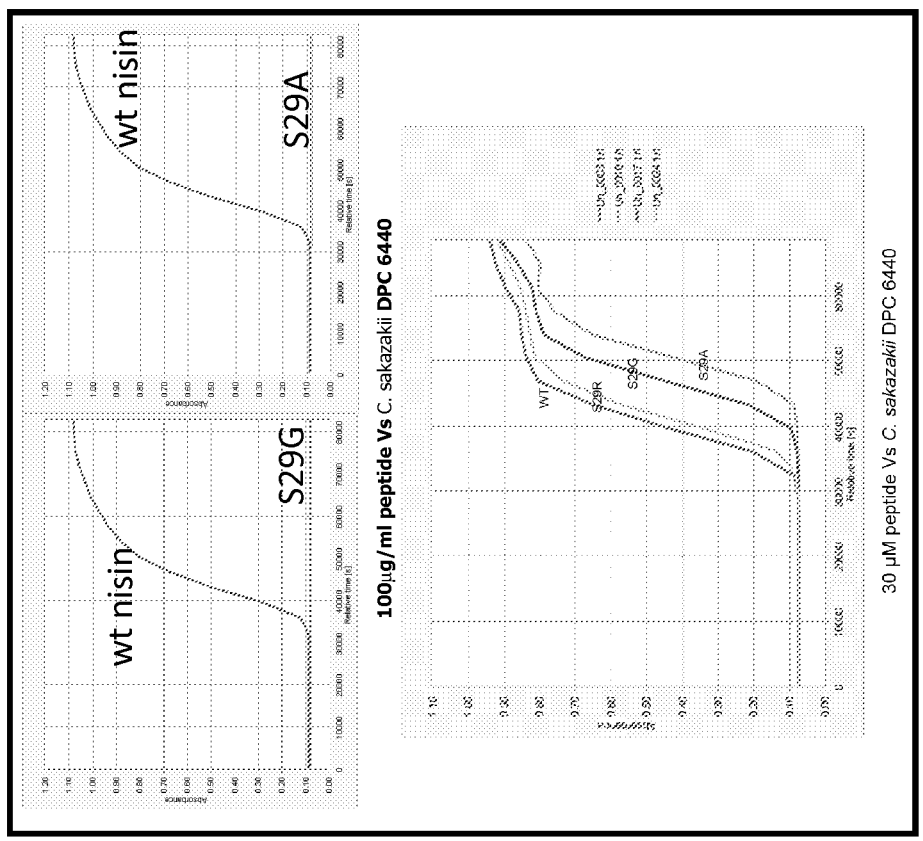
FIG. 2 illustrate a growth curve analysis of purified Nisin A and Nisin A S29G and S29A derivatives against *C. sakazakii* DPC6440 ($1\times10^5$ initial inoculum) at 100 μg/ml final concentration and of the same peptides, as well as Nisin A S29R, at a 30 μM concentration against the same target.

FIG. 2 shows growth curve analysis of purified Nisin A and Nisin A S29G and S29A derivatives against *C. sakazakii* DPC6440 ($1 \times 10^5$ initial inoculum) at 100 μg/ml final concentration. Results are representative of triplicate assays. The enhanced activity of these derivatives, and of Nisin A S29R, is also evident at a 30 μM final concentration.

Kill Curve Analysis of S29 Derivatives Against *C. sakazakii*

On the basis of growth curve and well assay analysis, kill curves were carried out using two concentrations of wild-type and S29G, S29A and S29R peptides (Table 9).

TABLE 9

Kill curve (1 hr) results of Nisin S29 mutants and Wt against *C. sakazakii* DPC 6440 ($1 \times 10^5$).

| | 54 μM | 30 μM | 6 μM |
|---|---|---|---|
| Nisin A | $1.0 \times 10^4$ | $4.0 \times 10^3$ | $8 \times 10^3$ |
| S29G | $3.0 \times 10^2$ | $5 \times 10^2$ | $1.0 \times 10^3$ |
| S29A | $7 \times 10^2$ | $1.0 \times 10^2$ | $6 \times 10^2$ |
| S29R | $2.0 \times 10^3$ | $1.6 \times 10^3$ | $1.0 \times 10^3$ |

Additional *C. sakazakii* Isolates from Powdered Infant Formula (PIF)

Modified agarose assays were carried out with 11 additional *C. sakazakii*. For this assay resuspended purified peptide is inoculated into wells which have been bored in the appropriate solid media plates (to which has been added the phosphate buffer washed indicator strain at a concentration of approx. $1 \times 10^7$) and allowed to incubate for 3 hours prior to overlay and overnight incubation at the desired temperature.

Modified Agarose Assay Method:

The media is made up fresh, autoclaved (121° C. for 15 mins) and cooled to 50° C. prior to use as follows: LB underlay 100 ml sodium phosphate buffer, 0.03 g LB, 1 g agarose and 20 uL Tween 20. LB Overlay: 100 ml H2O 5 g LB and 1 g agarose.

A fresh overnight of the target indicator is re-inoculated (2%) and allowed to grow for approx 3 hours to early log phase (OD ~0.3). 1 ml early log phase cells are washed twice in sodium phosphate buffer by centrifuging at 12,000 rpm for 6 min. The cells are resuspended in 1 ml buffer to reach a final concentration of approx $1 \times 10^7$. 100 μl of cells are added to 15 mls of LB underlay, poured into a small petri dish (9 cm) and allowed to set to form a uniform layer before punching wells (approx 5 mm) in the media. 10 μl of peptide is added at the desired concentration (30 μM) and the plates incubated at the appropriate temperature (i.e 37° C.) for 3 hours. Following this, the plates are overlayed with 15 mls of media (i.e. LB overlay), allowed to set and incubated at the appropriate temperature for 24 hours. Zones are measured using a vernier callipers after 24 hours.

Those peptides displaying enhanced activity are indicated by bold text.

TABLE 10

Modified agarose assays of Nisin derivatives against *C. sakazakii* PIF isolates (values represent zone size in mm)

| Cronobacter sakazakii strain | NisinA | S29G | S29A | S29D | S29E | S29R |
|---|---|---|---|---|---|---|
| DPC 6448 | 8.4 | 9.8 | 10.4 | 8.3 | 12.3 | 8.0 |
| DPC6445 | nz | Nz | nz | nz | nz | nz |
| DPC6444 | 6.2 | 6.3 | 6.8 | nz | 8.6hazy | nz |
| DPC6443 | nz | 6.4 | 6.8 | nz | 7.4 | nz |
| DPC6442 | 8.0 | 9.5 | 9.4 | 7.4 | 8.6 | nz |
| DPC6441 | nz | 7.5 | 8.2 | nz | 9.0 | nz |
| DPC6522 | nz | 7.5 | 7.7 | nz | 8.0hazy | nz |
| DPC 6440 | 6.53 | 7.56 | 7.50 | nz | 6.96 | 7.03 |
| DPC6442 | 10.1 | 11.16 | 11.40 | 9.90 | 10.13 | 9.13 |
| DPC6446 | 10.03 | 11.06 | 10.40 | 10.83 | 11.06 | 9.06 |
| DPC6524 | 8.93 | 9.63 | 9.10 | 8.83 | 8.92 | 7.60 | nz = no zone of inhibition

The results indicate that Nisin A S29G and S29A are consistently better than Nisin A against *C. sakazakii* isolates, with Nisin A S29D, S29E and S29R being enhanced in some instances.

Activity Against Additional Infant Milk Formula (IMF) Isolates

Standard deferred antagonism (spot on lawn) assays were performed on 7 isolates from infant milk formula Table. 11

TABLE 11

Assessment of the activity Nisin A S29 derivatives against a selection of other infant milk formula associated strains

| STRAIN | NisinA (mm) | S29G (mm) | S29A (mm) | S29D (mm) | S29E (mm) | S29R (mm) |
|---|---|---|---|---|---|---|
| Bacillus cereus IMF4 | 7.5 | 8.1 | 8.6 | NZ | 7.2 | 7.2 |
| Staphylococcus hominis IMF12 | 18.5 | 19.6 | 20.8 | 20.0 | 17.6 | 13.7 |
| Staphylococcus epidermidis IMF54 | 10.0 | 12.3 | 12.1 | 6.9 | 9.4 | 7.9 |
| Bacillus firmus IMF68 | 18.8 | 18.0 | 19.6 | 20.3 | 18.3 | 13.9 |
| Enterococcus durans IMF90 | 16.3 | 17.8 | 16.6 | 17.9 | 17.3 | 9.4 |
| Enterococcus faecium IMF91 | 14.1 | 17.0 | 16.4 | 16.5 | 10.8 | 9.3 |

Average of duplicate results

Nisin A, Z, F and Q Mutants
Saturation of Serine-29 in Nisin A, Z, F and Q Backgrounds and S29-I30 Combination in Nisin A Background
Nisin A S29 Derivatives As has been previously outlined, randomization of the codon at serine 29 of the nisA gene produced several derivatives with enhanced bioactivity namely S29G, S29A, S29D, S29E and S29R. The latter was recently discovered through the use of a modified overlay and growth curve assay using producing strain supernatants.

Figure 3:
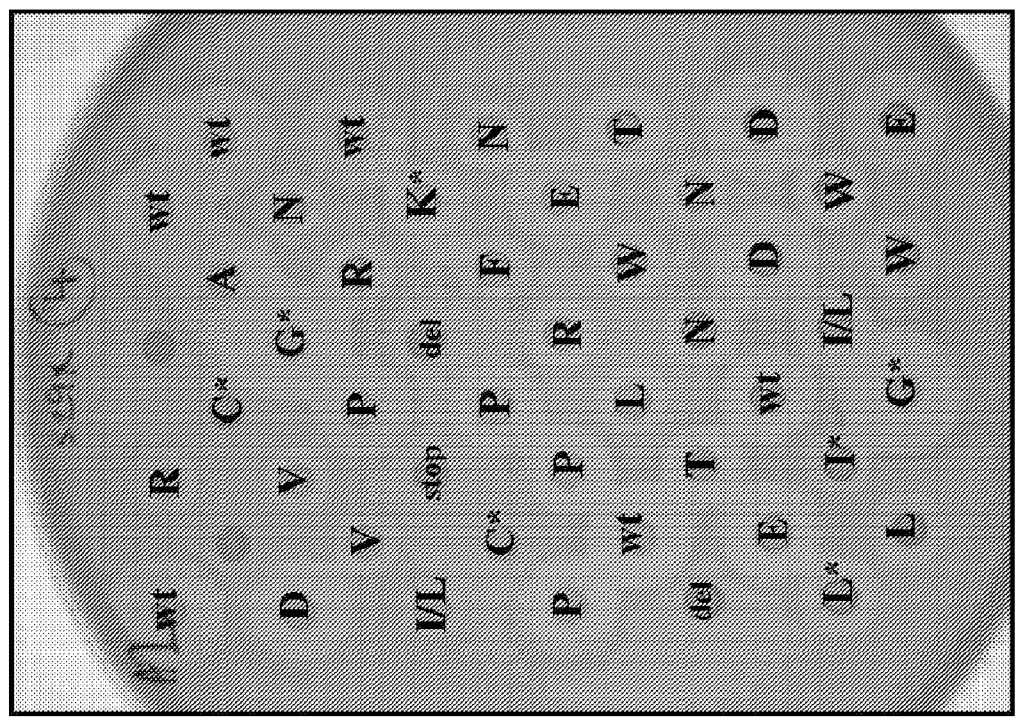
FIG. 3 illustrates a photo of the deferred antagonism assays of Nisin A-S29X variants against *L. lactis* HP.

FIGS. 1 and 3 shows the results of deferred antagonism assays of NisinA-S29X variants against *L. lactis* HP. Amino acid changes are indicated by the single letter code and were determined by Mass Spectrometry. The symbol * denotes amino acid change determined by DNA sequence analysis.

Nisin Z S29X Derivatives

Saturation mutagenesis of the serine codon at position 29 of nisZ was carried out with pDF05 (pCI372-nisA) as template and using oligonucleotides NisZS29deg FOR5' Pho-GCA ACT TGT AAC TGT NNK ATT CAC GTA AGC AAA TAA TCT AGA and NisZS29deg REV 5' GCT TAC GTG AAT MNN ACA GTT ACA AGT TGC TGT TTT CAT GTT containing an NNK codon in place of each native codon (codons to alter His27Asn are underlined). The purified products were subsequently introduced by electroporation into the strain NZ9800 which has all the genes necessary for Nisin production. Approximately 180 transformants were chosen at random and inoculated into 96 well plates containing GM17 chloramphenicol, incubated overnight and stored at −20° C. after addition of 80% glycerol.

Screening of the bank was carried out using deferred antagonism assays using *Lactococcus lactis* HP, *S. aureus* RF122 (FIG. 4) and *Listeria monocytogenes* LO28.

Figure 4:
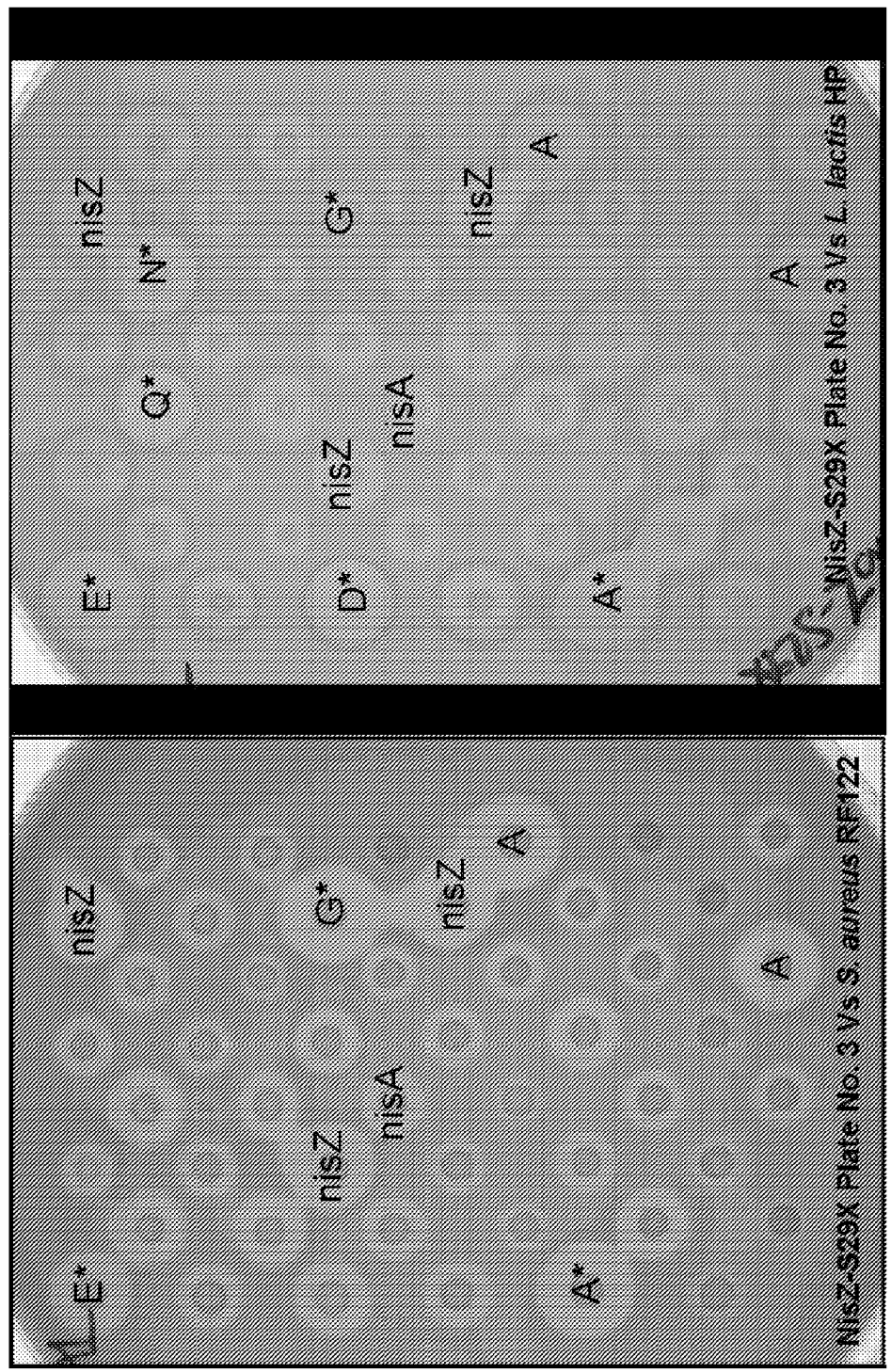
FIG. 4 illustrates the results of deferred antagonism assays of Nisin Z-S29X variants against *S. aureus* RF122 and *L. lactis* HP.

FIG. 4. Deferred antagonism assays of NisinZ-S29X variants against *S. aureus* RF122 and *L. lactis* HP. Amino acid changes are indicated by the single letter code and were determined by Mass Spectrometry. * denotes amino acid change determined by DNA sequence analysis.

Summary

S29G and S29A derivatives are still enhanced in the Nisin Z background when tested against both strains *L. lactis* HP and *S. aureus* RF122. Interestingly, Nisin A was included as a control and it is observed that Nisin A<Nisin Z<NisinZ S29A/S29G when tested against *S. aureus* RF122. The apparent lack of activity of NisinZ-S29G against *L. lactis* HP is still under investigation. The Nisin Z S29E, S29D but also S29N derivatives show enhanced activity against *L. lactis* HP which for S29E and S29D is also observed in the Nisin A background. However, S29N in Nisin A is not enhanced.

Nisin F S29X Derivatives

Saturation mutagenesis of the serine codon at position 29 of nisZ was carried out with pDF05 (pCI372-nisA) as template and using oligonucleotides NisFS29deg FOR5' Pho-GCA ACT TGT AAC TGT NNK GTT CAC GTA AGC AAA TAA TCT AGA and NisFS29deg REV 5' GCT TAC GTG AAC MNN ACA GTT ACA AGT TGC TGT TTT CAT GTT containing an NNK codon in place of each native codon (codon changes for H27N and I30V are underlined). The purified products were subsequently introduced by electroporation into the strain NZ9800 which has all the genes necessary for Nisin production. Approximately 180 transformants were chosen at random and inoculated into 96 well plates containing GM17 chloramphenicol, incubated overnight and stored at −20° C. after addition of 80% glycerol.

Screening of the bank was carried out using deferred antagonism assays using *Lactococcus lactis* HP (FIG. 5), *S. aureus* RF122 and *Listeria monocytogenes* LO28.

Figure 5:
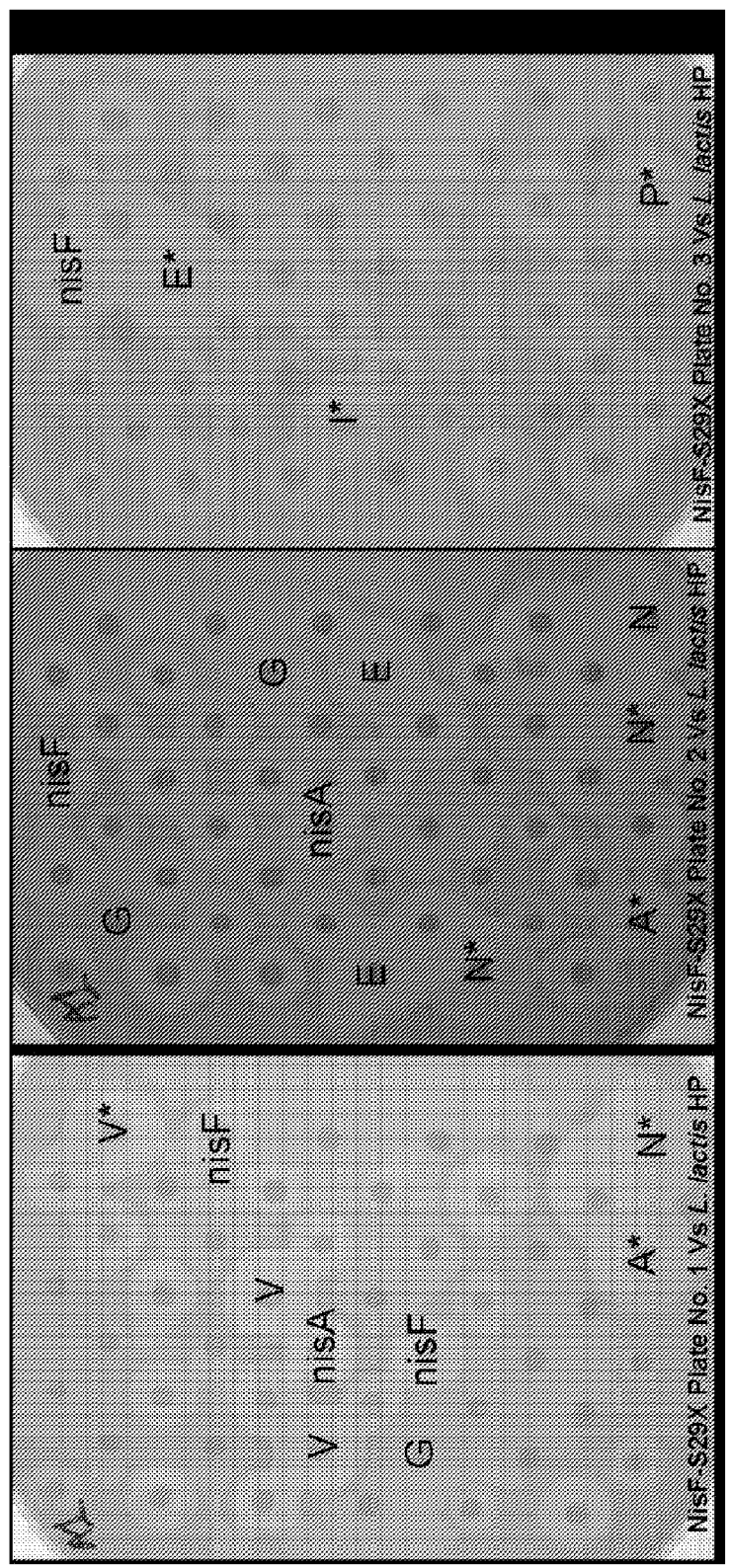
FIG. 5 illustrate the results of deferred antagonism assays of Nisin F-S29X variants against *L. lactis* HP.

FIG. 5 shows the results of deferred antagonism assays of NisinF-S29X variants against *L. lactis* HP. Amino acid changes are indicated by the single letter code and were determined by Mass Spectrometry. The symbol * denotes amino acid change determined by DNA sequence analysis.

Summary

S29E and S29A derivatives are still enhanced in the Nisin F background when tested against the strain *L. lactis* HP. Wild-type Nisin A was included as a control and it is observed that Nisin A<Nisin F<Nisin F S29E, and S29A. Moreover, S29V and S29N are enhanced in the Nisin F background, while S29D could not be detected. Importantly, Nisin F S29G appears to be greatly reduced in activity. A mass corresponding to S29G was observed several times, yet all exhibited little/no activity. The reason for this is not yet apparent, though S29G in the Nisin Z background also displayed poor activity against *L. lactis* HP only (FIG. 4).

Nisin Q S29X Derivatives

Saturation mutagenesis of the serine codon at position 29 of nisQ was carried out with pC1372-nisQ as template and using oligonucleotides NisFS29deg FOR5' Pho-GCA ACT TGT AAC TGT NNK GTT CAC GTA AGC AAA TAA TCT AGA 3' and NisQS29deg REV 5' GCT TAC GTG AAC MNN ACA GTT ACA AGT TGC TGT TTT CAG 3' containing an NNK codon in place of each native codon (codon changes for H27N and I30V and M21L are underlined). The purified products were subsequently introduced by electroporation into the strain NZ9800 which has all the genes necessary for Nisin production. Approximately 180 transformants were chosen at random and inoculated into 96 well plates containing GM17 chloramphenicol, incubated overnight and stored at −20° C. after addition of 80% glycerol.

Screening of the bank was carried out using deferred antagonism assays using *Lactococcus lactis* HP (FIG. 6), *S. aureus* RF122 and *Listeria monocytogenes* LO28.

Figure 6:
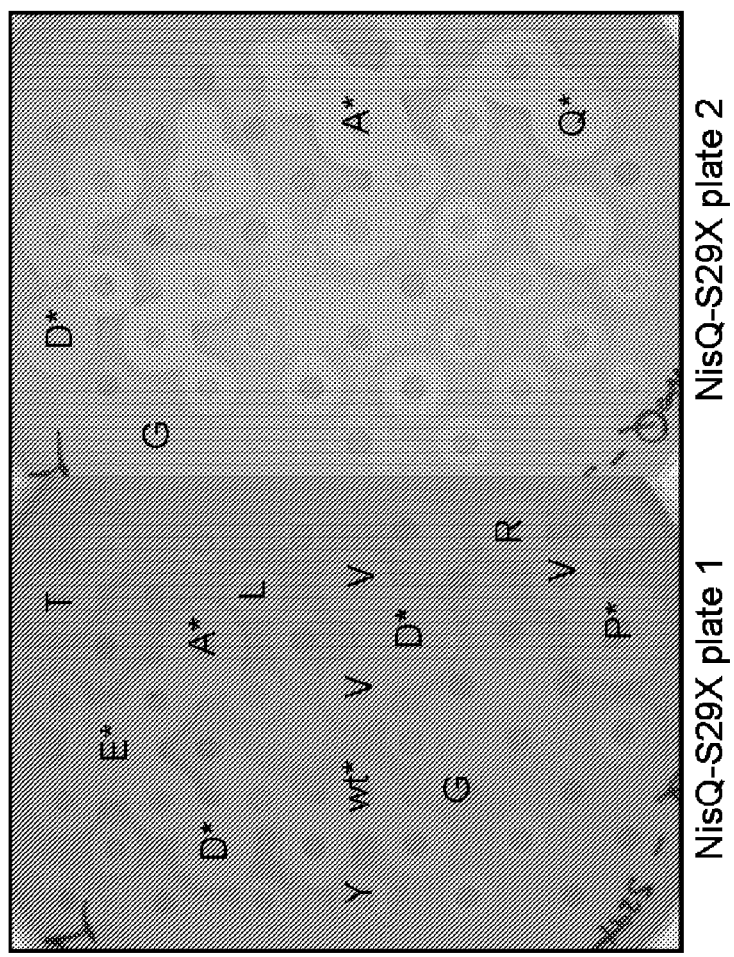
FIG. 6 illustrate the results of deferred antagonism assays of Nisin Q-S29X variants against *L. lactis* HP.

FIG. 6. Deferred antagonism assays of NisinQ-S29X variants against *L. lactis* HP. Amino acid changes are indicated by the single letter code and were determined by Mass Spectrometry.

denotes amino acid change determined by DNA sequence analysis.

Summary

The Nisin Q S29D, S29E and S29A derivatives all show enhanced activity against *L. lactis* HP. S29A is also enhanced against *S. aureus* RF122. Interestingly, Nisin Q S29G exhibits very reduced activity (FIG. 6) and this was also found to be the case for Nisin F S29G (FIG. 5). Given that Nisin F and Nisin Q are identical at the C-terminus (H27N, I30V), amino acid substitutions at serine 29 would be expected to have similar outcomes for bioactivity in each case. Indeed, enhanced derivatives S29D, S29E, S29A are detected in each background. One exception appears to be Nisin F S29V which exhibits enhanced activity, while Nisin Q S29V exhibits a wild-type phenotype. In contrast, S29P exhibits an enhanced phenotype in the Nisin Q, but not Nisin F backgrounds.

The consequences, with respect to the mass of the peptide produced, of subjecting Nisin A, Z, F and Q to saturation mutagenesis at position 29 are summarised in Table 12.

TABLE 12

S29X derivatives identified in NisinA, NisinZ, NisinF and NisinQ backgrounds.

| Amino acid | NisinA-S29X | NisinZ-S29X | NisinF-S29X | NisinQ-S29X |
|---|---|---|---|---|
| N | 3379.66 | 3358.92 | 3341.45 | nd |
| Q | 3393.69 | 3372.41 | Nd | 3367.38 |
| C | 3368.70 | Nd | Nd | nd |
| G | 3322.60 | 3300.64 | 3286.77 | 3299.07 |
| A | 3336.64 | 3314.55 | 3299.41 | 3311.85 |
| S | 3353.15 (WT) | 3331.63 (WT) | 3316.85 (WT) | 3327.50 (WT) |
| T | 3366.66 | 3344.91 | 3329.03 | 3342.64 |
| V | 3364.69 | 3343.08 | 3327.44 | 3340.10 |
| L | 3378.71 | 3356.42 | 3341.95 | 3353.85 |
| I | 3378.71 | 3356.06 | 3340.50 | 3353.85 |
| P | 3362.67 | 3341.27 | 3326.56 | 3338.64 |
| M | 3396.74 | 3374.82 | 3360.86 | nd |
| F | 3412.73 | 3390.79 | 3376.60 | nd |
| Y | 3428.73 | 3407.16 | 3394.39 | 3403.74 |
| W | 3451.76 | 3429.48 | 3415.04 | nd |
| D | 3380.64 | 3355.30 | 3343.60 | 3354.11 |
| E | 3394.67 | 3373.15 | 3357.93 | 3367.97 |
| R | 3421.74 | 3399.69 | 3385.13 | 3397.29 |

TABLE 12-continued

S29X derivatives identified in NisinA, NisinZ, NisinF and NisinQ backgrounds.

| Amino acid | NisinA-S29X | NisinZ-S29X | NisinF-S29X | NisinQ-S29X |
|---|---|---|---|---|
| H | 3402.69 | Nd | 3364.28 | 3376.93 |
| K | 3393.72 | 3372.66 | Nd | nd | nd—derivative not detected

Nisin A S29XX Derivatives (in which Serine 29 and Isoleucine 30 are Randomized Together).

As a consequence of the altered activity of serine 29 derivatives in the Nisin F background (which differs from Nisin A at positions 27 and 30: His27Asn, Ile30Val), randomization of serine 29 and isoleucine 30 in combination was carried out in the Nisin A background.

Saturation mutagenesis of the serine and isoleucine codons at position 29 and 30 respectively of nisA was carried out with pDF05 (pCI372-nisA) as template and using oligonucleotides NisAS29XXdeg FOR5' Pho-TGT CAT TGT NNK NNK CAC GTA AGC AAA TAA TCT AGA and NisAS29XXdeg REV 5' GCT TAC GTG MNN MNN ACA TAG ACA AGT TGC TGT TTT CAT GTT containing an NNK codon in place of each native codon. The purified products were subsequently introduced by electroporation into the strain NZ9800 which has all the genes necessary for Nisin production. Approximately 2000 transformants were chosen at random and inoculated into 96 well plates containing GM17 freezing buffer with chloramphenicol (10 μg/ml) incubated overnight and stored at −20° C.

Figure 7:
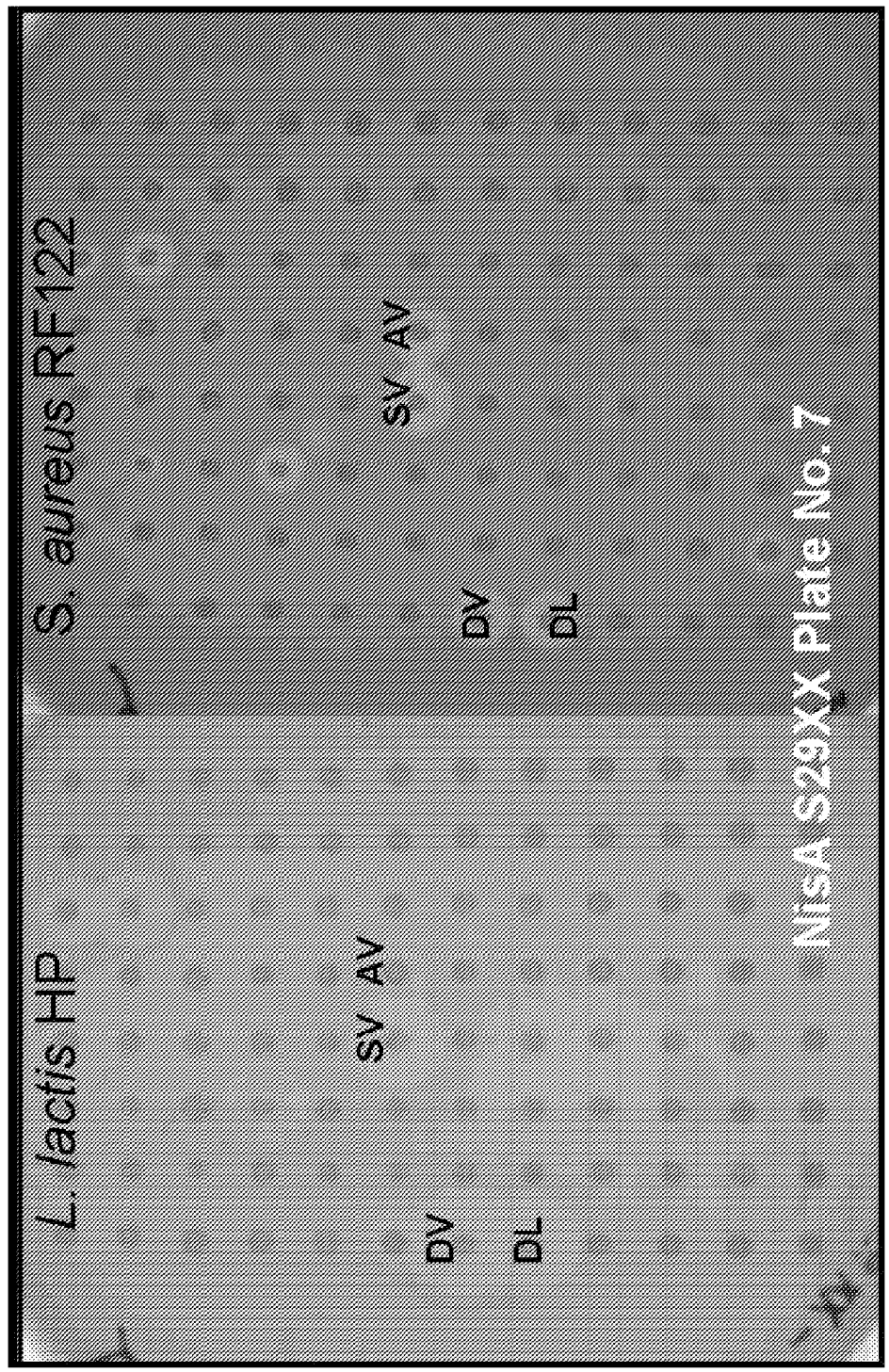
FIG. 7 illustrates the results of deferred antagonism assays of select Nisin A-S29XX variants against *L. lactis* HP and *S. aureus* RF122.

Screening of the bank was carried out using deferred antagonism assays using *Lactococcus lactis* HP, and *S. aureus* RF122 (FIG. 7).

FIG. 7 shows the results of deferred antagonism assays of select NisinA-S29XX variants against *L. lactis* HP and *S. aureus* RF122. The symbol * denotes amino acid change determined by DNA sequence analysis.

Summary

From the approximately 2000 mutants screened, 10 mutants exhibiting the strongest zones of inhibition (against one or all the indicator strains tested) were selected for DNA sequence analysis as mass spectrometry alone cannot be used to determine amino acid substitutions where two or more codons are altered simultaneously. The amino acid substitutions and target strain activity in each case are listed in Table. 13.

TABLE 13

Nisin 29-30 mutants generated through saturation mutagenesis which show potent antimicrobial activity.

| Serine29X | Isoleucine30X | L. lactis HP | S. aureus RF122 | L. mono LO28 |
|---|---|---|---|---|
| D | V | ✓ | | |
| D | L | ✓ | | |
| D | I | ✓ | ✓ | ✓ |
| A | V | | ✓ | |
| E | L | ✓ | ✓ | ✓ |
| E | A | ✓ | | |
| S | G | ✓ | | |
| S | V | ✓ | ✓ | ✓ |
| N | L | ✓ | | |

These investigations further highlight the benefits in many instances of having an alanine (A), aspartate (D), glutamate (E), or asparagine (N). Among the combinations generated were those noted above as being enhanced i.e. DI, corresponding to the Ser29Asp derivative of Nisin A, and DV, corresponding to the Ser29Asp derivative of Nisin F, and AV, corresponding to the Ser29Ala derivative of Nisin F.

Alanine at position 29 was also detected, in combination with valine 30, which correlates with an equivalent Nisin F S29A derivative exhibiting enhanced activity (FIG. 5.)

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The invention claimed is:

1. A Nisin derivative comprising a Nisin variant comprising an amino acid substitution resulting in a G, A, E, D, R, P, N, or V amino acid at the 29 position of the amino acid sequence, wherein the Nisin derivative exhibits an enhanced antimicrobial activity compared to a Nisin peptide without an amino acid substitution at position 29.

2. The Nisin derivative of claim 1 comprising at least one further amino acid substitution at amino acid position 30 in the amino acid sequence.

3. The Nisin derivative of claim 1 wherein the Nisin variant is selected from the group consisting of: Nisin A, Nisin Z, Nisin F and Nisin Q.

4. The Nisin derivative of claim 2 wherein the further amino acid substitution results in a Valine (V), Leucine (L), Isoleucine (I), Alanine (A), Glycine (G) at amino acid position 30 of the amino acid sequence.

5. A method of treating a disease caused by bacterial infection, the method comprising administering to a subject the Nisin derivative of claim 1.

6. The method of claim 5, wherein the disease is at least one of bovine mastitis, dental plaque, gastric ulcers, CDAD (*Clostridum difficile* associated diarrhoea), acne, or bacterial infections.

7. A pharmaceutical composition, comprising the Nisin derivative of claim 1 together with a pharmaceutically acceptable carrier or excipient.

8. A food additive comprising the Nisin derivative of claim 1.

9. A nucleotide sequence encoding the Nisin derivative of claim 1.

10. An expression vector comprising a nucleotide sequence encoding the Nisin derivative of claim 1.

11. A host cell expressing the Nisin derivative of claim 1.

12. The Nisin derivative of claim 1, wherein the natural variant is Nisin A.

13. The Nisin derivative of claim 12, wherein the natural variant is Nisin A and the substitution is S29G.

14. The Nisin derivative of claim 12, wherein the natural variant is Nisin A and the substitution is S29A.

15. The Nisin derivative of claim 12, wherein the natural variant is Nisin A and the substitution is S29E.

16. The Nisin derivative of claim 12, wherein the natural variant is Nisin A and the substitution is S29D.

17. The Nisin derivative of claim 12, wherein the natural variant is Nisin A and the substitution is S29R.

18. The Nisin derivative of claim 1, wherein the natural variant is Nisin F.

19. The Nisin derivative of claim 18, wherein the natural variant is Nisin F and the substitution is S29A.

20. The Nisin derivative of claim 18, wherein the natural variant is Nisin F and the substitution is S29E.

21. The Nisin derivative of claim 18, wherein the natural variant is Nisin F and the substitution is S29V.

22. The Nisin derivative of claim 18, wherein the natural variant is Nisin F and the substitution is S29N.

23. The Nisin derivative of claim 1, wherein the natural variant is Nisin Q.

24. The Nisin derivative of claim 23, wherein the natural variant is Nisin Q and the substitution is S29A.

25. The Nisin derivative of claim 23, wherein the natural variant is Nisin Q and the substitution is S29D.

26. The Nisin derivative of claim 23, wherein the natural variant is Nisin Q and the substitution is S29E.

27. The Nisin derivative of claim 23, wherein the natural variant is Nisin Q and the substitution is S29P.

28. The Nisin derivative of claim 1, wherein the natural variant is Nisin Z.

29. The Nisin derivative of claim 28, wherein the natural variant is Nisin Z and the substitution is S29G.

30. The Nisin derivative of claim 28, wherein the natural variant is Nisin Z and the substitution is S29D.

31. The Nisin derivative of claim 28, wherein the natural variant is Nisin Z and the substitution is S29E.

32. The Nisin derivative of claim 28, wherein the natural variant is Nisin Z and the substitution is S29N.

33. A Nisin variant comprising a S29X substitution, wherein the Nisin variant is Nisin A, Nisin F, Nisin Q, Nisin Z Nisin U, and Nisin U2, wherein X is G, A, E, D, Q, R, V, P, W, T, N, I, L, C, or M.

\* \* \* \* \*